US012575975B2

(12) United States Patent
Locke et al.

(10) Patent No.: US 12,575,975 B2
(45) Date of Patent: Mar. 17, 2026

(54) SYSTEMS AND METHODS FOR SENSING PROPERTIES OF FLUIDS FROM A TISSUE SITE

(71) Applicant: Solventum Intellectual Properties Company, Maplewood, MN (US)

(72) Inventors: Christopher Brian Locke, Bournemouth (GB); Justin Alexander Long, Lago Vista, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 857 days.

(21) Appl. No.: 17/762,872

(22) PCT Filed: Sep. 24, 2020

(86) PCT No.: PCT/IB2020/058965
§ 371 (c)(1),
(2) Date: Mar. 23, 2022

(87) PCT Pub. No.: WO2021/059209
PCT Pub. Date: Apr. 1, 2021

(65) Prior Publication Data
US 2022/0354702 A1     Nov. 10, 2022

Related U.S. Application Data

(60) Provisional application No. 62/905,859, filed on Sep. 25, 2019.

(51) Int. Cl.
*A61F 13/05* (2024.01)
*A61M 1/00* (2006.01)
(52) U.S. Cl.
CPC .............. *A61F 13/05* (2024.01); *A61M 1/73* (2021.05); *A61M 1/90* (2021.05); *A61M 1/915* (2021.05);
(Continued)

(58) Field of Classification Search
CPC ............ A61M 1/73; A61M 1/90; A61M 1/95; A61M 1/96; A61M 1/98; A61M 1/962;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion for Corresponding Application No. PCT/IB2020/058965 mailed Feb. 11, 2021.
(Continued)

*Primary Examiner* — Alireza Nia
*Assistant Examiner* — Andrew Jun-Wai Mok

(57) ABSTRACT

Systems, apparatuses, and methods for providing negative pressure to a tissue site are disclosed. Some embodiments are illustrative of an apparatus or system for delivering negative-pressure to a tissue site that can be used in conjunction with sensing properties of fluids extracted from a tissue site. For example, an apparatus may comprise a dressing interface or connector that includes a pH sensor, a humidity sensor, a temperature sensor and/or a pressure sensor embodied on a single pad within the connector and proximate the tissue site to provide data indicative of acidity, humidity, temperature and pressure. Such apparatus may further comprise an ambient port for providing the pressure sensor and the humidity sensor with access to the ambient environment providing readings relative to the atmospheric pressure and humidity.

22 Claims, 13 Drawing Sheets

(52) U.S. Cl.
CPC ....... *A61M 1/92* (2021.05); *A61M 2205/3324*
(2013.01); *A61M 2205/3368* (2013.01)

(58) Field of Classification Search
CPC .......... A61M 1/966; A61M 2205/3324; A61M
2205/3344; A61F 13/00; A61F 13/00008;
A61F 13/00021; A61F 13/05; A61F
2013/00089
See application file for complete search history.

(56)                    References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |

| | | | |
|---|---|---|---|
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2010/0022990 | A1* | 1/2010 | Karpowicz ............. A61M 1/74 604/543 |
| 2011/0054283 | A1 | 3/2011 | Shuler |
| 2014/0163491 | A1 | 6/2014 | Schuessler et al. |
| 2015/0080788 | A1 | 3/2015 | Blott et al. |
| 2015/0320434 | A1* | 11/2015 | Ingram ................... A61M 1/85 606/131 |
| 2019/0082242 | A1* | 3/2019 | Duesterhoft ......... A61B 5/0015 |
| 2019/0216991 | A1* | 7/2019 | Locke .................. A61M 1/966 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |

(56) References Cited

FOREIGN PATENT DOCUMENTS

| | | | |
|---|---|---|---|
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2017195038 | A1 | 11/2017 |
| WO | 2017213752 | A1 | 12/2017 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56)                    References Cited

OTHER PUBLICATIONS

V.A. Solovev, Dissertation Abstract, Treatment and Prevention of
Suture Failures after Gastric Resection (S.M. Kirov Gorky State
Medical Institute, Gorky, U.S.S.R. 1988) ("Solovev Abstract").
V.A.C.® Therapy Clinical Guidelines: A Reference Source for
Clinicians; Jul. 2007.

* cited by examiner

SYSTEMS AND METHODS FOR SENSING PROPERTIES OF FLUIDS FROM A TISSUE SITE

CROSS-REFERENCE TO RELATED APPLICATIONS

This application claims the benefit of priority to U.S. Provisional Application No. 62/905,859, filed on Sep. 25, 2019, which is incorporated herein by reference in its entirety.

TECHNICAL FIELD

The invention set forth in the appended claims relates generally to tissue treatment systems and more particularly, but without limitation, to systems and methods for providing negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy and instillation therapy are widely known, improvements to therapy systems, components, and processes may benefit healthcare providers and patients.

BRIEF SUMMARY

New and useful systems, apparatuses, and methods for applying negative pressure to a tissue site using a dressing are set forth in the appended claims. Illustrative embodiments are also provided to enable a person skilled in the art to make and use the claimed subject matter. Some embodiments are illustrative of an apparatus or system for delivering negative-pressure to a tissue site, which can be used in conjunction with sensing properties of wound exudates extracted from a tissue site. For example, an apparatus may include a pH sensor, a humidity sensor, a temperature sensor and a pressure sensor embodied on a single pad proximate the tissue site to provide data indicative of acidity, humidity, temperature and pressure. Such apparatus may further comprise a pH sensor having a sensing portion adapted to be positioned between the dressing and the tissue site and a terminal portion electrically coupled to a microprocessor configured to detect properties of fluid present at the tissue site and to provide an output to the microprocessor based on the property detected. For example, the microprocessor may be configured to detect properties of a pH level of fluid present at the tissue site and provide a pH output indicating the pH level detected.

In some embodiments, the dressing may comprise a wound dressing including a foam layer and having a tissue-facing surface and an opposing surface, and a dressing interface having a housing including a therapy cavity and a component cavity containing a microprocessor and other electrical component fluidly isolated from the therapy cavity and the wound dressing. The dressing may further comprise a sensor having a sensing portion positioned on the tissue-facing surface that contacts the tissue site, a conductor portion coupled to the sensing portion and extending through a perforation in the wound dressing, and a terminal portion positioned on the opposing surface and coupled to the conductor portion, wherein the terminal portion may be configured to be electrically coupled to the microprocessor. The dressing may further comprise a drape having an opening exposing the terminal portion and configured to cover and be coupled to the opposing surface of the wound dressing to fluidly isolate the terminal portion from the wound dressing and the perforation.

The dressing may further comprise an electrical connector adapted to electrically couple the terminal portion to the electrical component. The electrical connector may include an electrical pad coupled to the terminal portion and an electrical contact disposed on the dressing interface, wherein the electrical contact is electrically coupled to the electrical component and releasably connectable to the electrical pad. The dressing may also comprise a mechanical coupler adapted to couple the dressing interface to the wound dressing and enhance the continuity of the electrical connector. The mechanical connector may include a magnetic attachment coupled to the terminal portion and a magnet disposed on the dressing interface within the therapy cavity and is releasably engageable to the mechanical attachment. Alternatively, the mechanical connector may include a releasably engageable coupling device having a first part coupled to the terminal portion and a second part disposed on the dressing interface within the therapy cavity.

In some embodiments, the dressing interface may further comprise a port into the therapy cavity of the dressing interface that is adapted to be fluidly coupled to a negative-pressure source and the therapy cavity in fluid communication with the wound dressing. The dressing interface may further comprise a vent port fluidly coupled to the therapy cavity and adapted to enable airflow into the therapy cavity. The dressing interface may further comprise a temperature sensor and a humidity sensor, each sensor having a sensing portion disposed within the therapy cavity and electrically coupled to the microprocessor through the body of the housing.

In another embodiment of a dressing for treating a tissue site, the dressing may comprise a wound dressing having an upper layer comprising a foam and a lower layer having a tissue-facing surface, wherein the lower layer is adapted to be positioned between the upper layer and the tissue site. The dressing may further comprise a pH sensor having a sensing portion positioned on the tissue-facing surface of the lower layer that is adapted to contact the tissue site. The pH sensor may further include and a conductor portion coupled to the sensing portion and extending through a perforation in the wound dressing so that the perforation is fluidly isolated from the tissue site. The pH sensor may also include a terminal portion coupled to the conductor portion and configured to be electrically coupled to an electrical component disposed within a dressing interface.

Some embodiments are illustrative of a method of applying negative-pressure to a dressing for treating a tissue site. For example, the method may comprise positioning a tissue interface on the tissue site, wherein the tissue interface has a first layer comprising foam and a second layer comprising a plurality of apertures. In some embodiments, the second layer may be adapted to be positioned between the first layer and the tissue site. In some embodiments, the method may further comprise positioning a sensing portion of a pH sensor between the second layer and the tissue site and extending a conductor portion of the pH sensor through the tissue interface. The method may further comprise positioning a dressing interface adjacent the tissue interface wherein the dressing interface has a therapy cavity fluidly coupled to the first layer of the tissue interface and a component cavity fluidly isolated from the therapy cavity. The method may further comprise electrically coupling a terminal portion of the pH sensor to an electrical component disposed within the component cavity, such as a microprocessor, wherein the terminal portion is coupled to the conductor portion and disposed on the first layer. The method may further comprise applying negative pressure to the therapy cavity through a port to draw fluid from the tissue site into through the tissue interface.

Some embodiments are illustrative of applying negative-pressure to a tissue interface and sensing properties of fluid at a tissue site. In one example embodiment, the method may comprise positioning a dressing interface wherein the dressing interface comprises a housing having a body including a therapy cavity and a component cavity fluidly isolated from the therapy cavity, wherein the therapy cavity has an opening configured to be in fluid communication with the tissue interface. The dressing interface may further comprise a negative-pressure port fluidly coupled to the therapy cavity, an ambient port fluidly coupled to the component cavity, a control device disposed within the component cavity, and at least one sensor having a sensing portion disposed within the therapy cavity and coupled to the control device. The dressing interface may further comprise an ambient input fluidly coupled to the component cavity for providing the sensor access to the ambient environment. The method may further comprise applying negative pressure to the therapy cavity to draw fluids from the tissue interface and into the therapy cavity. The method may further comprise sensing properties of the ambient environment provided by the at least one sensor through the ambient input and the component cavity, and sensing properties of the fluids within the therapy cavity provided by the at least one sensor as compared to the properties of the ambient environment.

Objectives, advantages, and a preferred mode of making and using the claimed subject matter may be understood best by reference to the accompanying drawings in conjunction with the following detailed description of illustrative embodiments.

Figure 1:
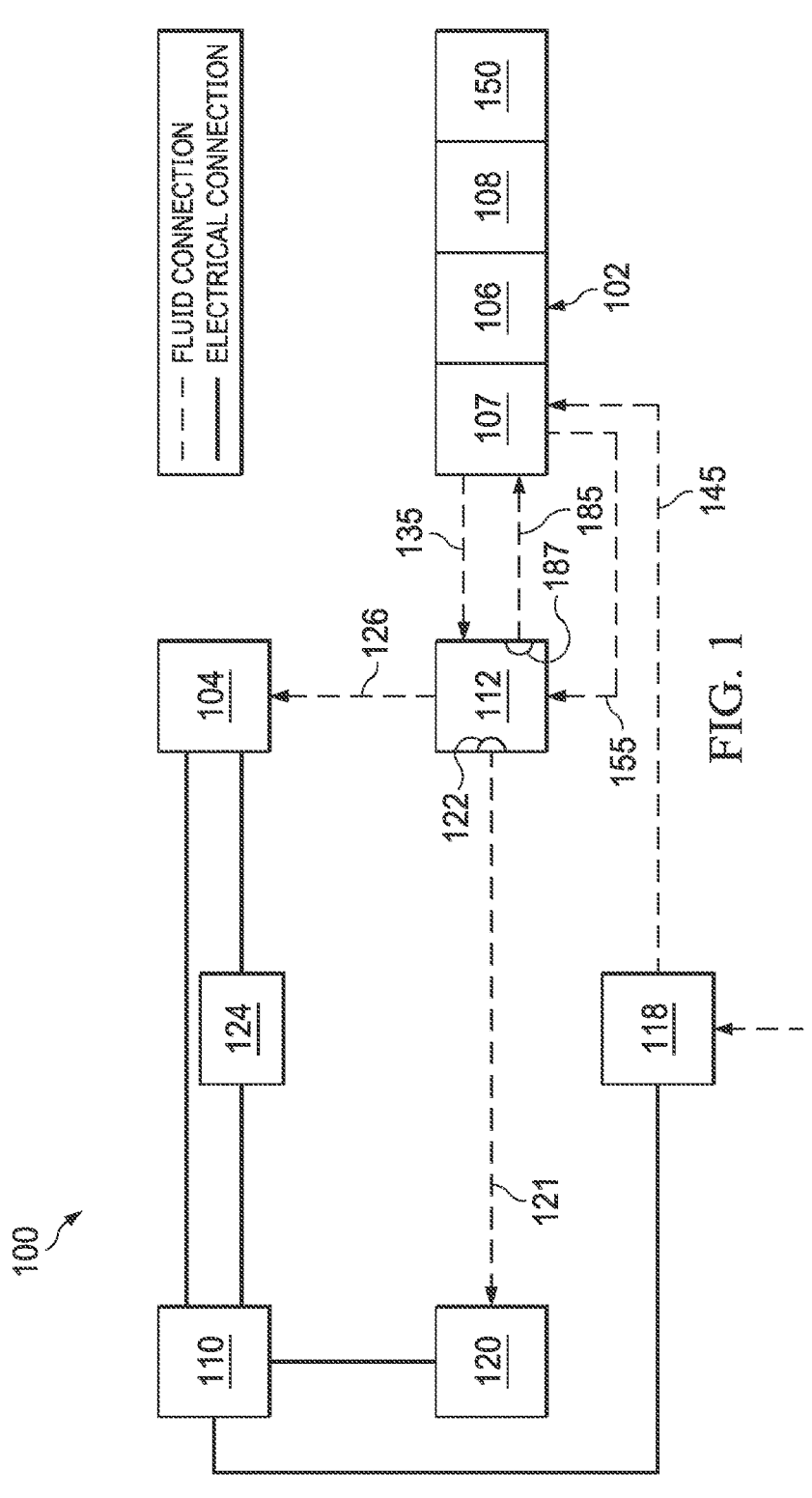
FIG. 1 is a functional block diagram of an example embodiment of a therapy system for providing negative-pressure including both instillation and venting capabilities in accordance with this specification.
Figure 3:
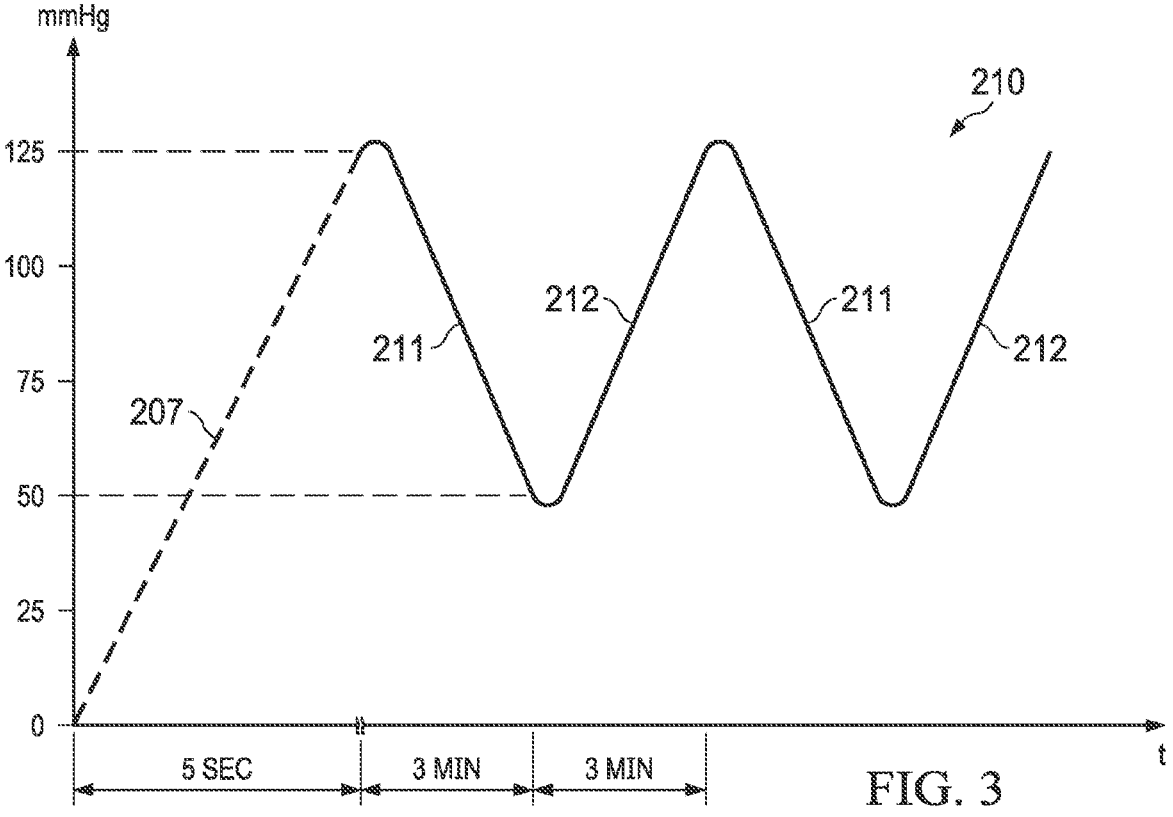
Figure 4:
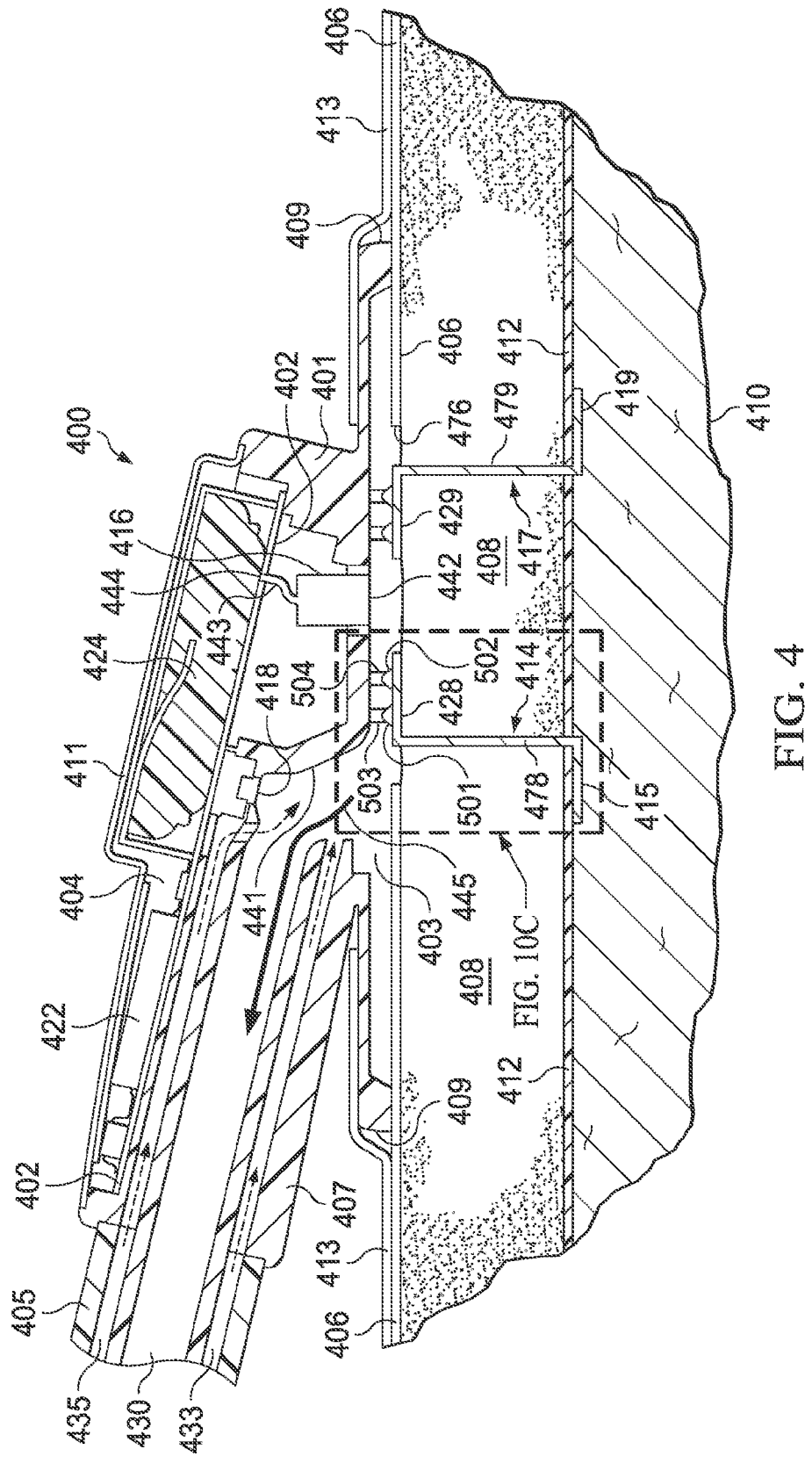
Figure 5A:
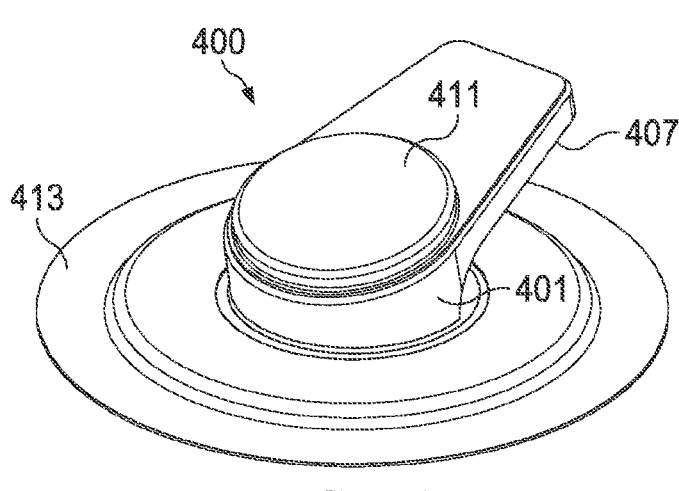
Figure 5B:
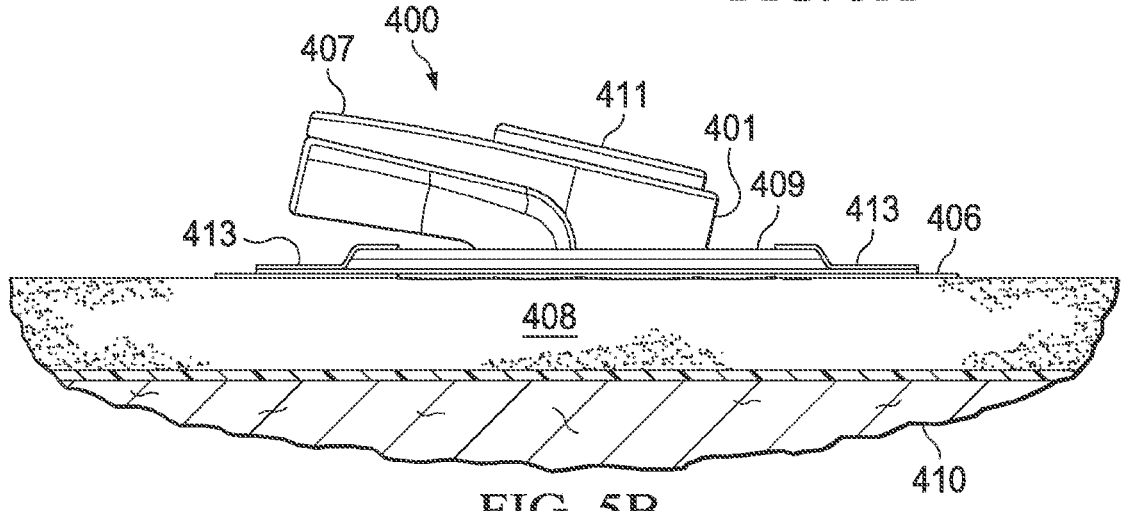
Figure 5C:
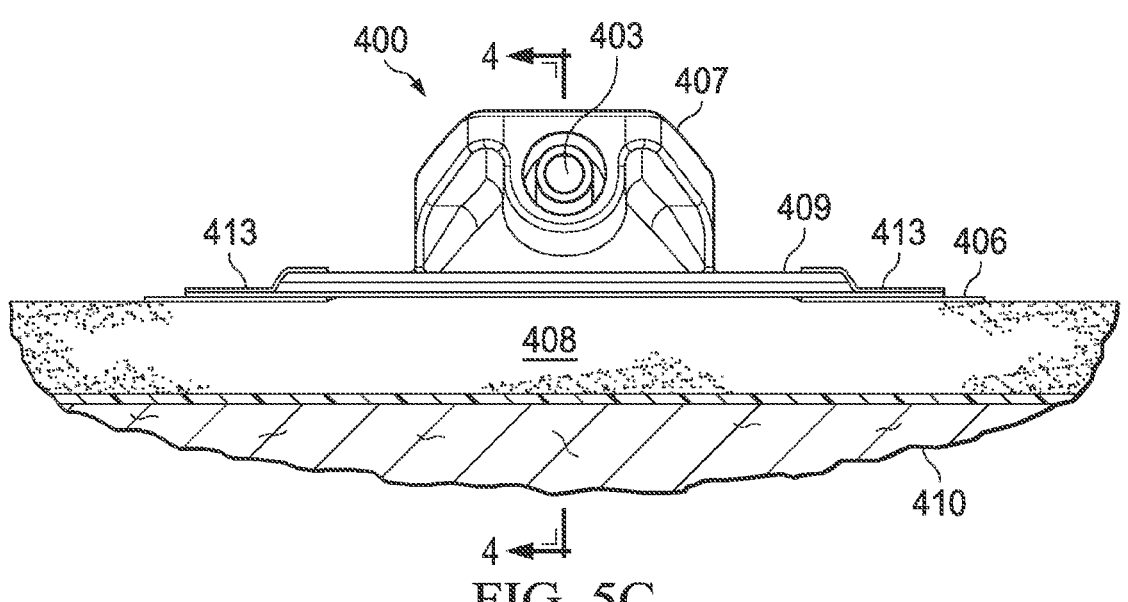
Figure 6A:
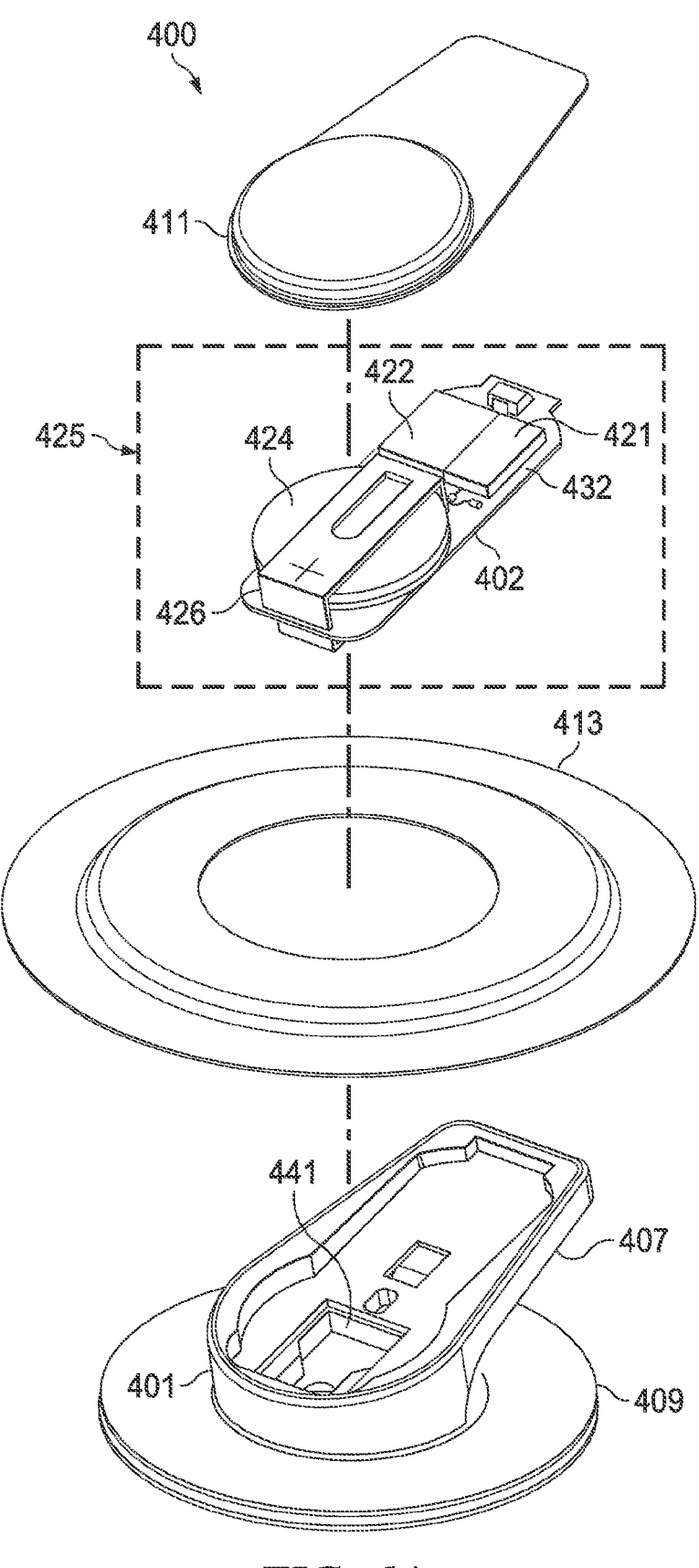
Figure 6B:
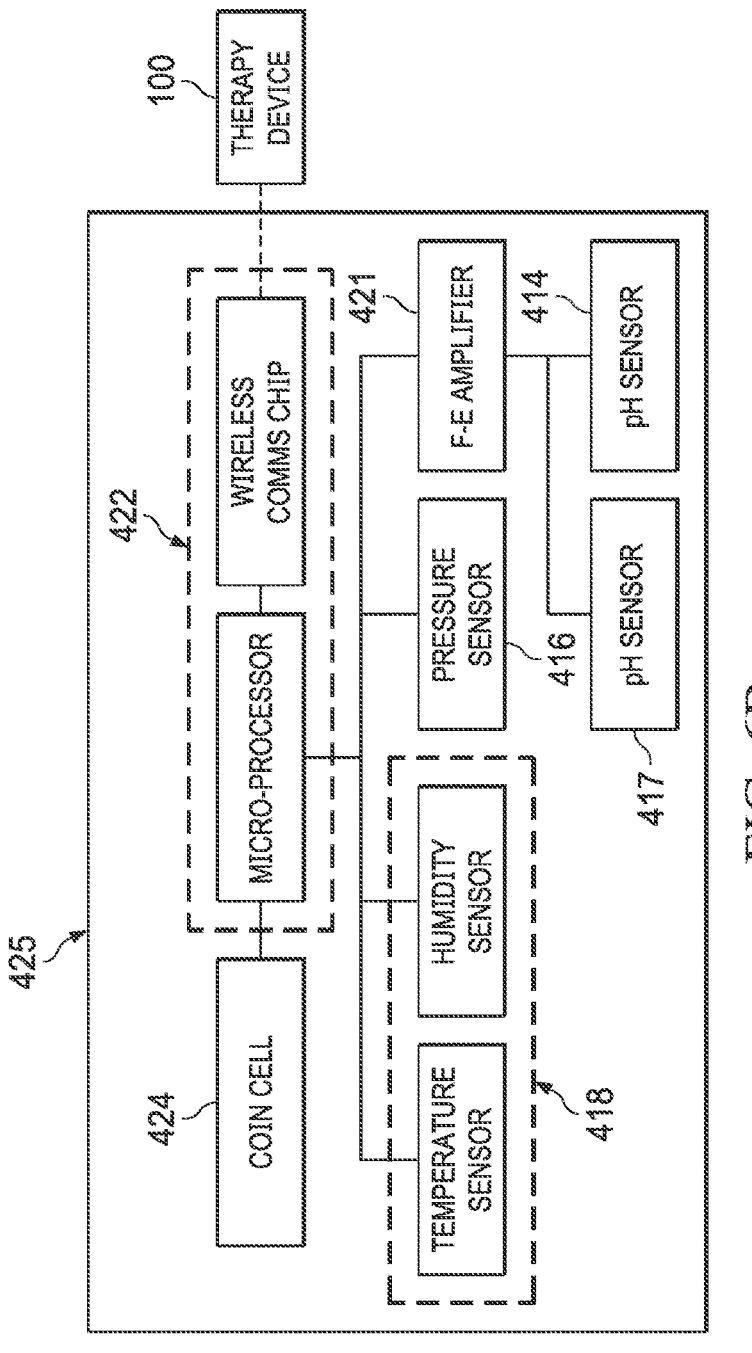
Figure 7A:
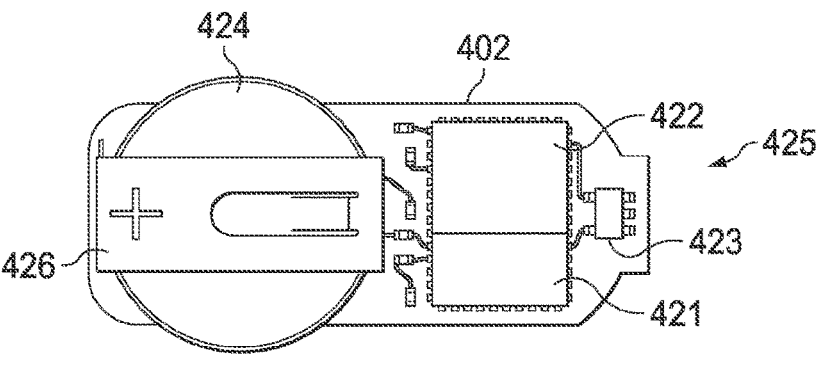
Figure 7B:
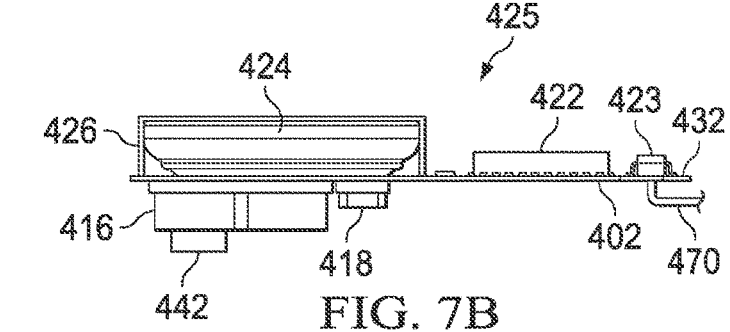
Figure 7C:
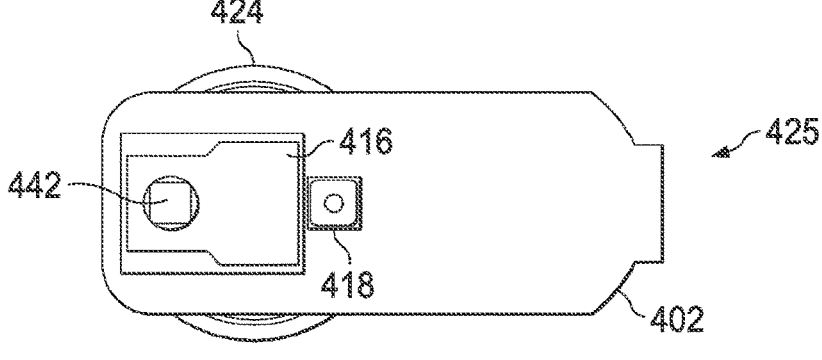
Figure 7D:
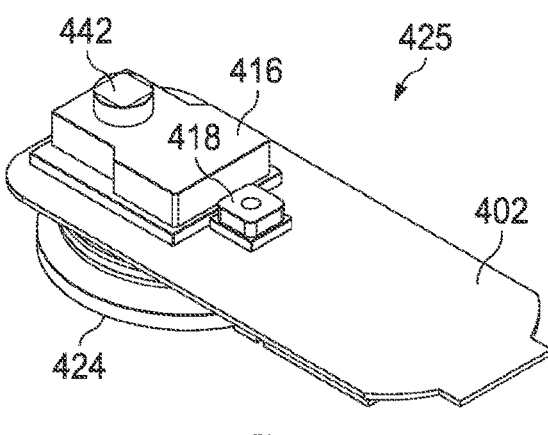
Figure 8A:
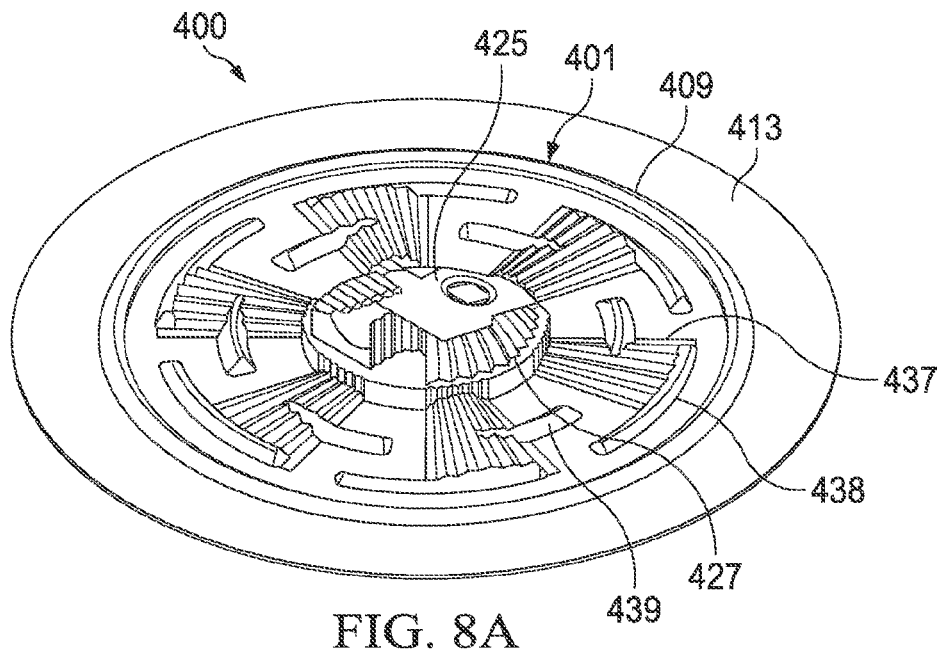
Figure 8B:
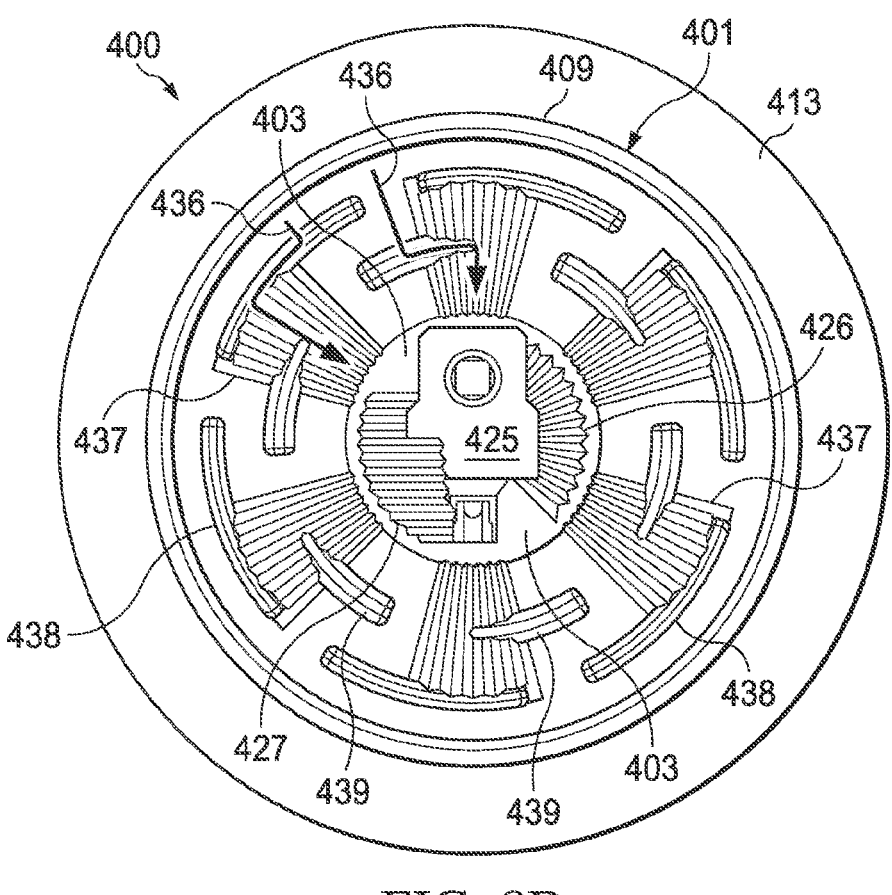
Figure 9A:
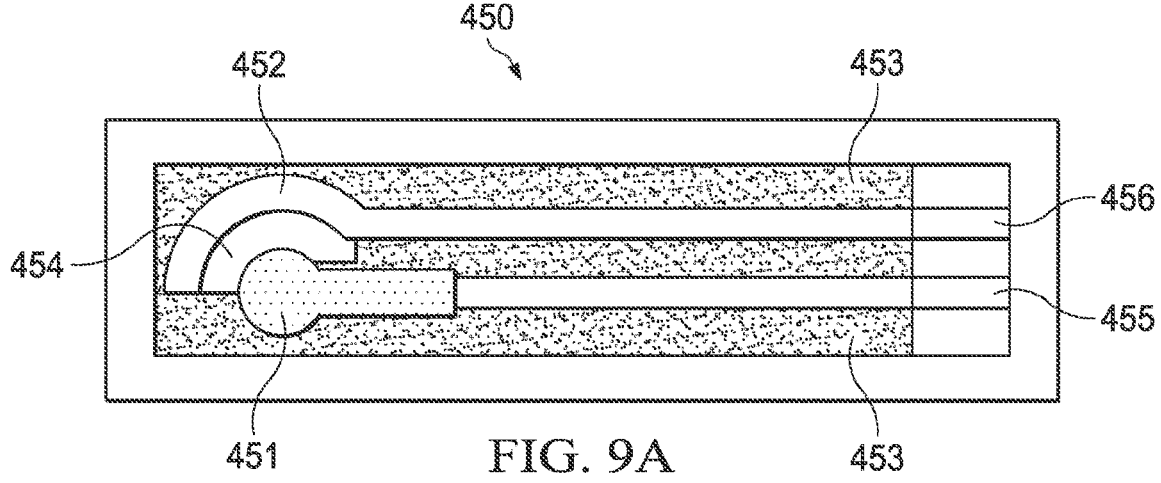
Figure 9B:
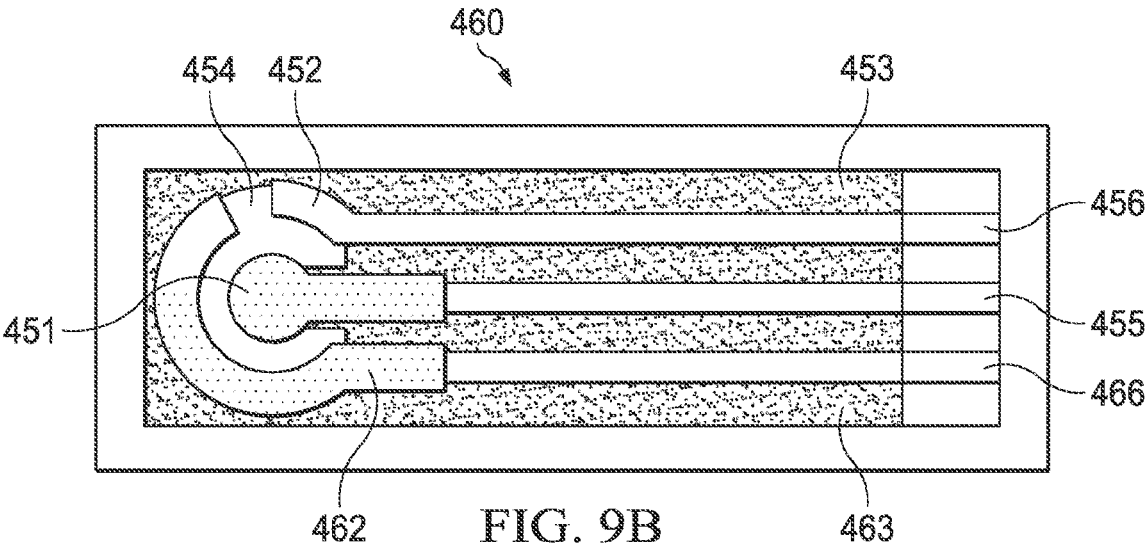
Figure 10A:
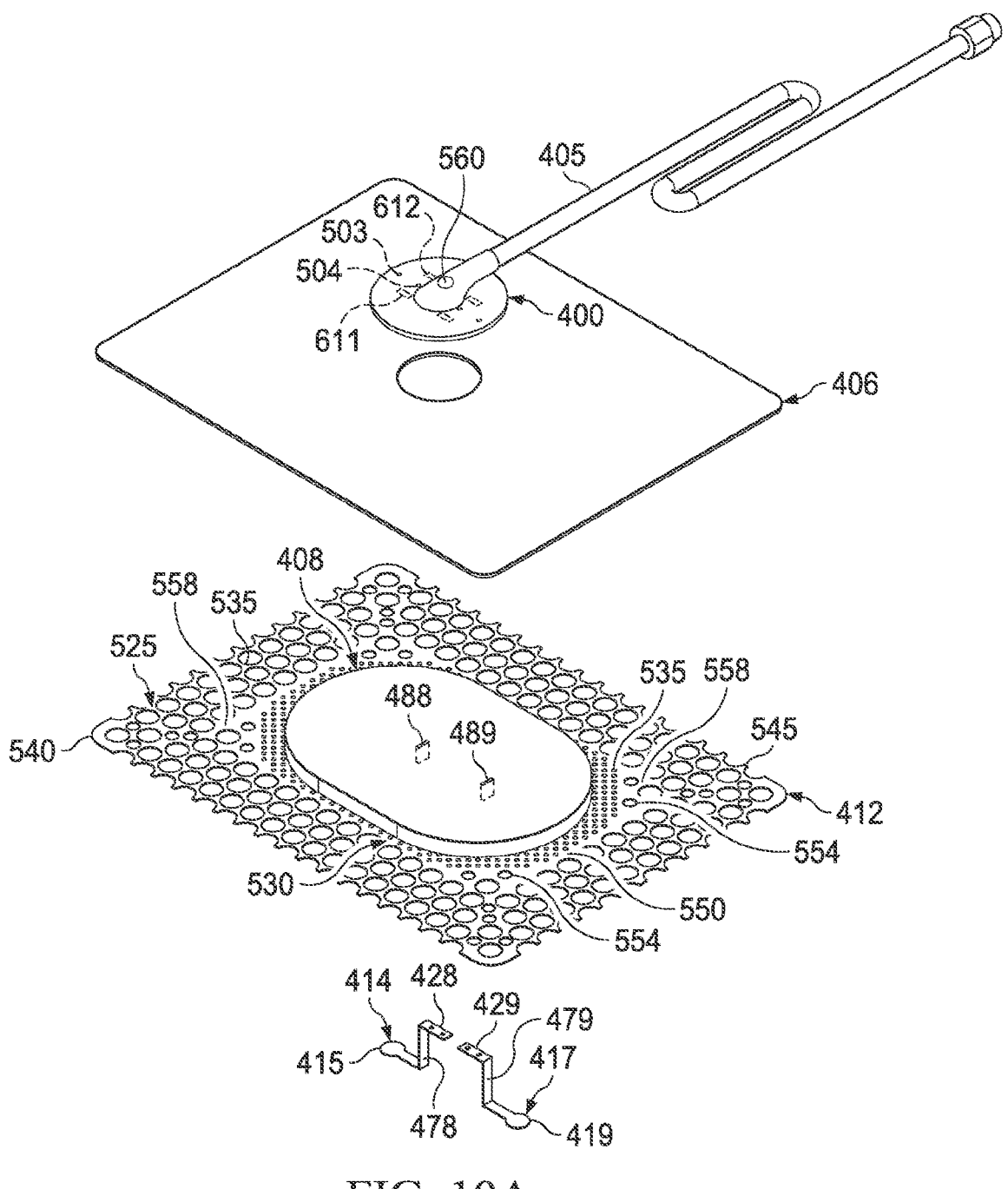
Figure 10B:
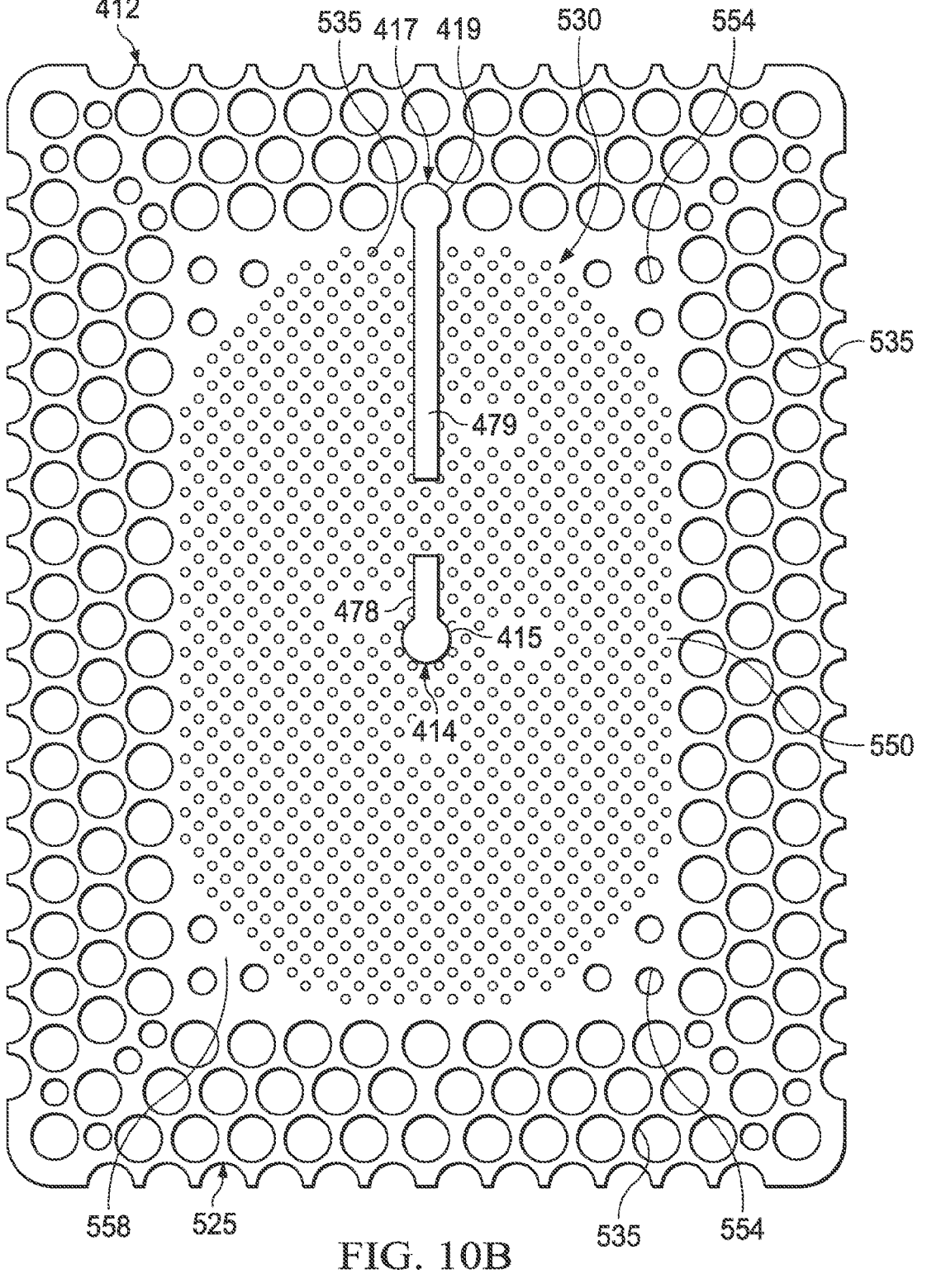
Figure 10C:
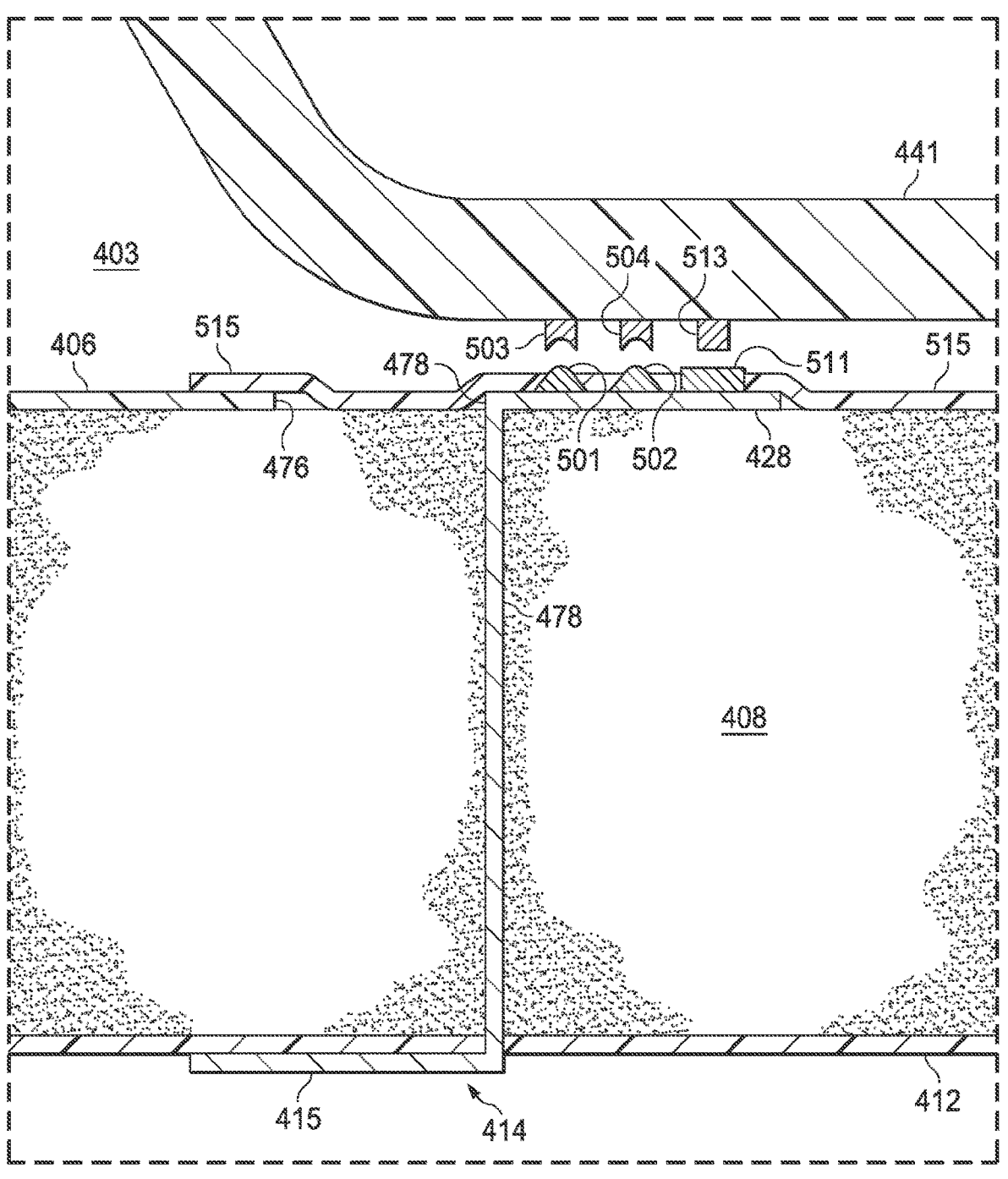
Figure 11:
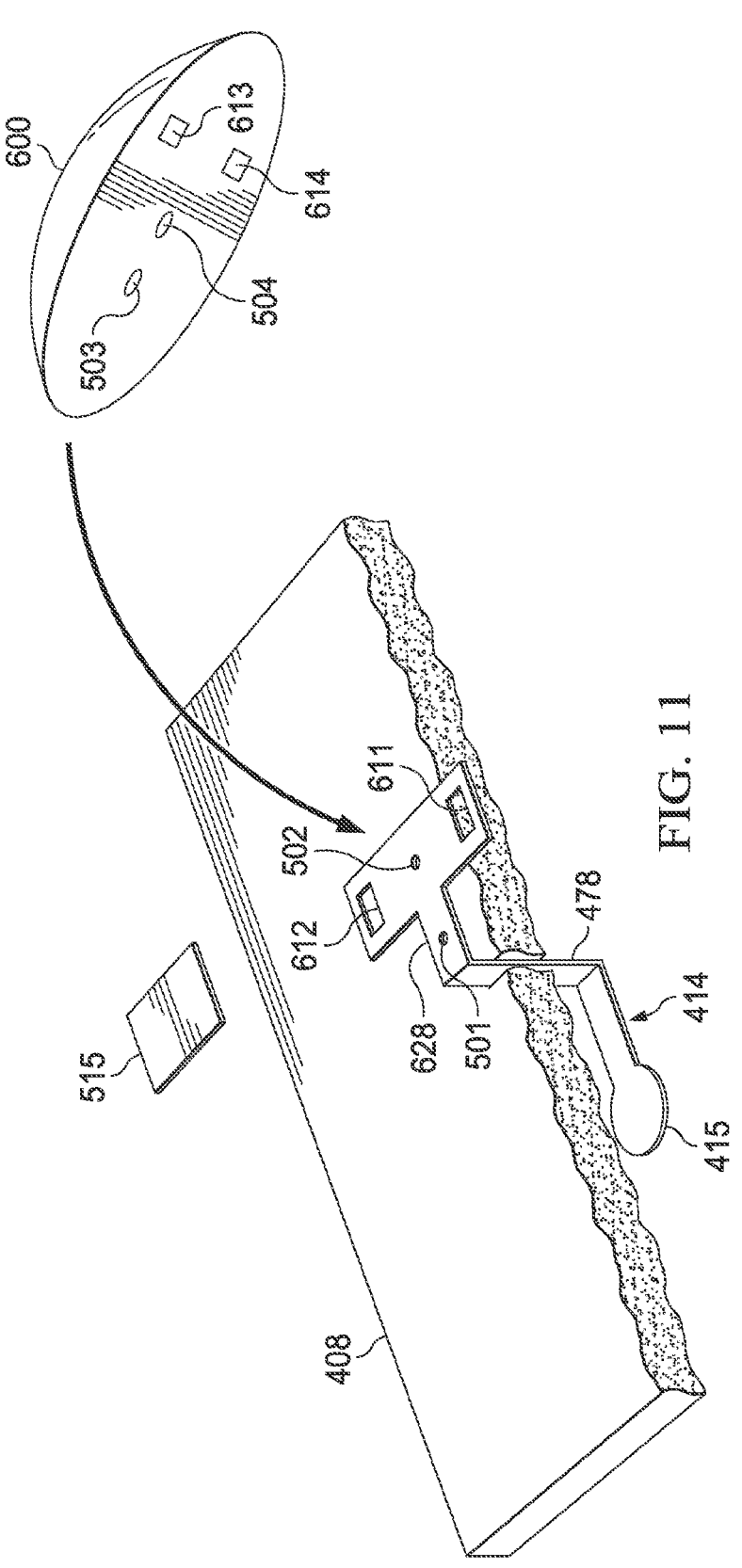

that varies with time in a continuous pressure mode and an intermittent pressure mode that may be used for applying negative pressure in the therapy system;

FIG. 3 is a graph illustrating an illustrative embodiment of another pressure control mode for the negative-pressure and instillation therapy system of FIG. 1 wherein the x-axis represents time in minutes (min) and/or seconds(sec) and the y-axis represents pressure generated by a pump in Ton (mmHg) that varies with time in a dynamic pressure mode that may be used for applying negative pressure in the therapy system;

FIG. 4 is a sectional side view of a dressing comprising a tissue interface having a manifold layer and a sealing layer including a plurality of apertures, a dressing interface having a housing including a therapy cavity and a component cavity, the therapy cavity having an opening adapted to be in fluid communication with the manifold layer of the tissue interface, and a pH sensor having a sensing portion adapted to be positioned between the sealing layer and the tissue site, wherein the dressing may be associated with some example embodiments of the therapy system of FIG. 1;

FIG. 5A is a perspective top view of the dressing of FIG. 4, FIG. 5B is a side view of the dressing of FIG. 4 disposed on a tissue site, and FIG. 5C is an end view of the dressing of FIG. 4 disposed on the tissue site;

FIG. 6A is an assembly view of the dressing interface of FIG. 4 comprising components of the housing and an example embodiment of a sensor assembly including a wall, sensors, and electrical devices;

FIG. 6B is a system block diagram of the sensors and electrical devices comprising the sensor assembly of FIG. 6A;

FIGS. 7A, 7B, 7C, and 7D are a top view, side view, bottom view, and perspective top view, respectively, of the sensor assembly of FIG. 6;

FIG. 8A is a perspective bottom view of the dressing interface of FIG. 4, and FIG. 8B is a bottom view of the dressing interface of FIG. 4;

FIG. 9A is a top view of a first embodiment of a pH sensor that may be used with the dressing of FIG. 4, and FIG. 9B is a top view of a second embodiment of a pH sensor that may be used with the dressing of FIG. 4;

FIG. 10A is an exploded perspective view of the dressing of FIG. 4;

FIG. 10B is a bottom view of the sealing layer portion of the dressing interface of FIG. 10A;

FIG. 10C is a detail view taken at reference FIG. 10C as depicted in FIG. 4 illustrating a portion of the tissue interface of FIG. 4 including a first embodiment of a pH sensor; and FIG. 11 is a perspective view of a portion of the tissue interface of FIG. 10A including a manifold and a second embodiment of a pH sensor, and a second dressing interface removed from the tissue interface.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The present technology also provides negative pressure therapy devices and systems, and methods of treatment using such systems with antimicrobial solutions. FIG. 1 is a simplified functional block diagram of an example embodiment of a therapy system 100 that can provide negative-pressure therapy with instillation of treatment solutions in accordance with this specification. The therapy system 100 may include a negative-pressure supply, and may include or be configured to be coupled to a distribution component, such as a dressing. In general, a distribution component may refer to any complementary or ancillary component configured to be fluidly coupled to a negative-pressure supply between a negative-pressure supply and a tissue site. A distribution component is preferably detachable, and may be disposable, reusable, or recyclable. For example, a dressing 102 is illustrative of a distribution component that may be coupled to a negative-pressure source and other components. The therapy system 100 may be packaged as a single, integrated unit such as a therapy system including all of the components shown in FIG. 1 that are fluidly coupled to the dressing 102.

The dressing 102 may be fluidly coupled to a negative-pressure source 104. A dressing may include a cover, a tissue interface, or both in some embodiments. The dressing 102, for example, may include a cover 106, a dressing interface 107, and a wound dressing or tissue interface 108. A computer or a controller device, such as a controller 110, may also be coupled to the negative-pressure source 104. In some embodiments, the cover 106 may be configured to cover the tissue interface 108 and the tissue site, and may be adapted to seal the tissue interface and create a therapeutic environment proximate to a tissue site for maintaining a negative pressure at the tissue site. In some embodiments, the dressing interface 107 may be configured to fluidly couple the negative-pressure source 104 to the therapeutic environment of the dressing. The therapy system 100 may optionally include a fluid container, such as a container 112, fluidly coupled to the dressing 102 and to the negative-pressure source 104.

The therapy system 100 also may include sensors to measure operating parameters and provide feedback signals to the controller 110 indicative of operating parameters of fluids extracted from a tissue site a month e.g., temperature, MMP, humidity, or pH. As illustrated in FIG. 1, for example, the therapy system 100 may include a pressure sensor 120, an electric sensor 124, or both, coupled to the controller 110. The pressure sensor 120 may be fluidly coupled or configured to be fluidly coupled to a distribution component such as, for example, the negative-pressure source 104 either directly or indirectly through the container 112. The pressure sensor 120 may be configured to measure pressure being generated by the negative-pressure source 104, i.e., the pump pressure (PP). The electric sensor 124 also may be coupled to the negative-pressure source 104 to measure the pump pressure (PP). In some example embodiments, the electric sensor 124 may be fluidly coupled proximate the output of the output of the negative-pressure source 104 to directly measure the pump pressure (PP). In other example embodiments, the electric sensor 124 may be electrically coupled to the negative-pressure source 104 to measure the changes in the current in order to determine the pump pressure (PP).

Distribution components may be fluidly coupled to each other to provide a distribution system for transferring fluids (i.e., liquid and/or gas). For example, a distribution system may include various combinations of fluid conductors and fittings to facilitate fluid coupling. A fluid conductor generally includes any structure with one or more lumina adapted to convey a fluid between two ends, such as a tube, pipe, hose, or conduit. Typically, a fluid conductor is an elongated, cylindrical structure with some flexibility, but the geometry and rigidity may vary. Some fluid conductors may be molded into or otherwise integrally combined with other components. A fitting can be used to mechanically and fluidly couple components to each other. For example, a fitting may comprise a projection and an aperture. The projection may be configured to be inserted into a fluid conductor so that the aperture aligns with a lumen of the fluid conductor. A valve is a type of fitting that can be used to control fluid flow. For example, a check valve can be used to substantially prevent return flow. A port is another example of a fitting. A port may also have a projection, which may be threaded, flared, tapered, barbed, or otherwise configured to provide a fluid seal when coupled to a component.

In some embodiments, distribution components may also be coupled by virtue of physical proximity, being integral to a single structure, or being formed from the same piece of material. Coupling may also include mechanical, thermal, electrical, or chemical coupling (such as a chemical bond) in some contexts. For example, a tube may mechanically and fluidly couple the dressing 102 to the container 112 in some embodiments. In general, components of the therapy system 100 may be coupled directly or indirectly. For example, the negative-pressure source 104 may be directly coupled to the controller 110, and may be indirectly coupled to the dressing interface 107 through the container 112 by conduit 126 and conduit 135, also referred to herein as negative pressure conduit 126 and negative pressure conduit 135. The pressure sensor 120 may be fluidly coupled to the dressing 102 directly (not shown) or indirectly through the container 112 and a filter 122 by conduit 121 and pressure sensing conduit 155. The filter 122 may be any type of filter for preventing the ingress of liquids from the container 112.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example. In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

Figure 2:
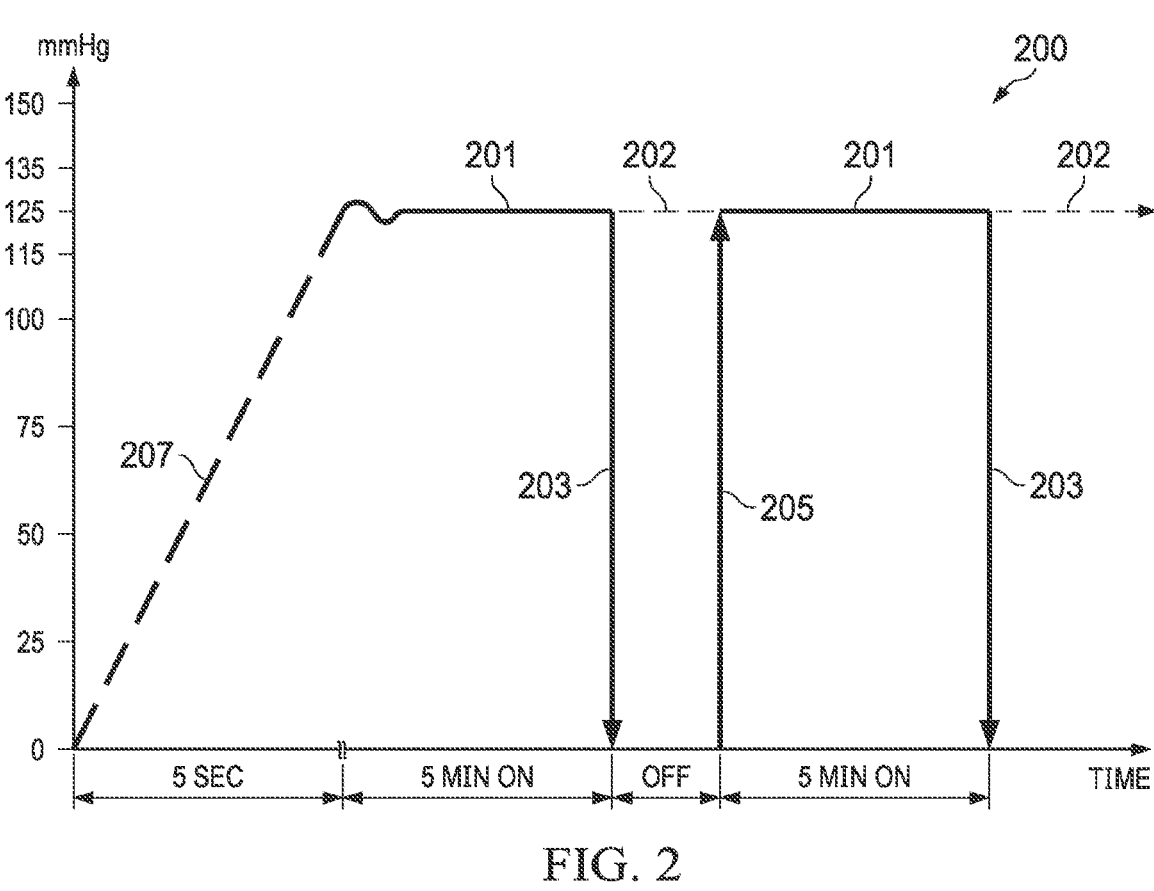
FIG. 2 is a graph illustrating an illustrative embodiment of pressure control modes for the negative-pressure and instillation therapy system of FIG. 1 wherein the x-axis represents time in minutes (min) and/or seconds(sec) and the y-axis represents pressure generated by a pump in Ton (mmHg)

Referring more specifically to FIG. 2, a graph illustrating an illustrative embodiment of pressure control modes 200 that may be used for the negative-pressure and instillation therapy system of FIG. 1 is shown wherein the x-axis represents time in minutes (min) and/or seconds (sec) and the y-axis represents pressure generated by a pump in Ton (mmHg) that varies with time in a continuous pressure mode and an intermittent pressure mode that may be used for applying negative pressure in the therapy system. The target pressure (TP) may be set by the user in a continuous pressure mode as indicated by solid line 201 and dotted line 202 wherein the wound pressure (WP) is applied to the tissue site 150 until the user deactivates the negative-pressure source 104. The target pressure (TP) may also be set by the user in an intermittent pressure mode as indicated by solid lines 201, 203 and 205 wherein the wound pressure (WP) is cycled between the target pressure (TP) and atmospheric pressure. For example, the target pressure (TP) may be set by the user at a value of 125 mmHg for a specified period of time (e.g., 5 min) followed by the therapy being turned off for a specified period of time (e.g., 2 min) as indicated by the gap between the solid lines 203 and 205 by venting the tissue site 150 to the atmosphere, and then repeating the cycle by turning the therapy back on as indicated by solid line 205 which consequently forms a square wave pattern between the target pressure (TP) level and atmospheric pressure. In some embodiments, the ratio of the "on-time" to the "off-time" or the total "cycle time" may be referred to as a pump duty cycle (PD).

In some example embodiments, the decrease in the wound pressure (WP) at the tissue site 150 from ambient pressure to the target pressure (TP) is not instantaneous, but rather gradual depending on the type of therapy equipment and dressing being used for the particular therapy treatment. For example, the negative-pressure source 104 and the dressing 102 may have an initial rise time as indicated by the dashed line 207 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system 100 is operating in the intermittent mode, the repeating rise time as indicated by the solid line 205 may be a value substantially equal to the initial rise time as indicated by the dashed line 207.

The target pressure may also be a variable target pressure (VTP) controlled or determined by controller 110 that varies in a dynamic pressure mode. For example, the variable target pressure (VTP) may vary between a maximum and minimum pressure value that may be set as an input determined by a user as the range of negative pressures desired for therapy at the tissue site 150. The variable target pressure (VTP) may also be processed and controlled by controller 110 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 150.

Referring more specifically to FIG. 3, a graph illustrating an illustrative embodiment of another pressure control mode for the negative-pressure and instillation therapy system of FIG. 1 is shown wherein the x-axis represents time in minutes (min) and/or seconds (sec) and the y-axis represents pressure generated by a pump in Torr (mmHg) that varies with time in a dynamic pressure mode that may be used for applying negative pressure in the therapy system. For example, the variable target pressure (VTP) may be a reduced pressure that provides an effective treatment by applying reduced pressure to tissue site 150 in the form of a triangular waveform varying between a minimum and maximum pressure of 50-125 mmHg with a rise time 212 set at a rate of +25 mmHg/min. and a descent time 211 set at −25 mmHg/min., respectively. In another embodiment of the therapy system 100, the variable target pressure (VTP) may be a reduced pressure that applies reduced pressure to tissue site 150 in the form of a triangular waveform varying between 25-125 mmHg with a rise time 212 set at a rate of +30 mmHg/min and a descent time 211 set at −30 mmHg/min. Again, the type of system and tissue site determines the type of reduced pressure therapy to be used.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may comprise a manifold such as manifold 408 shown in FIG. 4. A "manifold" in this context may include any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam manifold may vary according to needs of a prescribed therapy. For example, in some embodiments, the tissue interface 108 may be a foam manifold having pore sizes in a range of 400-600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or Vera-Flo® foam, both available from Kinetic Concepts, Inc. of San Antonio, Texas.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam° dressing available from Kinetic Concepts, Inc. of San Antonio, Texas. Other hydrophilic foams may include those made from polyether. Other foams that may exhibit hydrophilic properties include hydrophobic foams that have been treated or coated to provide hydrophilicity.

In some embodiments, the tissue interface 108 may be an absorbent pad. In some embodiments, the absorbent pad may be constructed from a laminate that includes an inner layer sandwiched between two outer layers. The inner layer may include a super absorbent polymer (SAP), such as cross-linked sodium polyacrylate absorbent with polyol and water. The outer layers may include cellulose, such as a tissue paper. The inner and outer layers are preferably laminated together using heat and pressure. The absorbent pad may include a minimum amount of adhesive and binders to secure the layers together, which allows the absorbent pad to include an even greater amount of sodium polyacrylate.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the tissue interface 108 may comprise a first layer or upper layer such as the manifold 408 and a second layer or lower layer such as a sealing layer 412 as shown in FIG. 4. In some embodiments, the first layer may be disposed adjacent to the second layer which may have a tissue-facing surface disposed adjacent the tissue site. For example, the first layer and the second layer may be stacked so that the first layer is in contact with the second layer. In some embodiments, the first layer may also be bonded to the second layer, which may be disposed adjacent the tissue site.

In some example embodiments, the sealing layer 412 may comprise or consist essentially of a soft, pliable material suitable for providing a fluid seal with a tissue site, and may have a substantially flat surface. For example, the sealing layer 412 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the sealing layer 412 may have a thickness between about 200 microns (μm) and about 1000 microns (m). In some embodiments, the sealing layer 412 may have a hardness between about 5 Shore OO and about 80 Shore OO. Further, the sealing layer 412 may be comprised of hydrophobic or hydrophilic materials. In some embodiments, the sealing layer 412 may be a hydrophobic-coated material. For example, the sealing layer 412 may be formed by coating a spaced material, such as, for example, woven, nonwoven, molded, or extruded mesh with a hydrophobic material. The hydrophobic material for the coating may be a soft silicone, for example.

Referring to FIG. 4 and FIGS. 10A-10B, the sealing layer 412 in one embodiment may comprise a peripheral area, such as a periphery 525, surrounding or disposed around a central area, such as an interior portion 530. The sealing layer 412 may further comprise apertures 535 extending through the periphery 525 and the interior portion 530. The interior portion 530 may correspond to a surface area of the manifold 408 in some examples. The sealing layer 412 may also have corners 540 and edges 545. The corners 540 and the edges 545 may be part of the periphery 525. The sealing layer 412 may have an interior border 550 around the interior portion 530, disposed between the interior portion 530 and the periphery 525. In some embodiments, the interior border 550 may be substantially free of the apertures 535, such as illustrated in the example of FIGS. 10A-10B. In some embodiments, the interior portion 530 may be symmetrical and centrally disposed in the sealing layer 412.

The apertures 535 may be formed by cutting or by application of local RF or ultrasonic energy, for example, or by other suitable techniques for forming an opening. The apertures 535 may have a uniform distribution pattern, or may be randomly distributed on the sealing layer 412. The apertures 535 in the sealing layer 412 may have many shapes, including circles, squares, stars, ovals, polygons, slits, complex curves, rectilinear shapes, triangles, for example, or may have some combination of such shapes. Each of the apertures 535 may have uniform or similar geometric properties. For example, in some embodiments, each of the apertures 535 may be circular apertures, having substantially the same diameter. In some embodiments, the diameter of the apertures 535 may be between about 1 millimeter and about 50 millimeters. In other embodiments, the diameter of the apertures 535 may be between about 1 millimeter and about 20 millimeters.

In other embodiments, geometric properties of the apertures 535 may vary. For example, the diameter of the apertures 535 may vary depending on the position of the apertures 535 in the sealing layer 412. In some embodiments, the diameter of the apertures 535 in the periphery 525 of the sealing layer 412 may be larger than the diameter of the apertures 535 in the interior portion 530 of the sealing layer 412. For example, in some embodiments, the apertures 535 disposed in the periphery 525 may have a diameter between about 9.8 millimeters to about 10.2 millimeters. In some embodiments, the apertures 535 disposed in the corners 540 may have a diameter between about 7.75 millimeters to about 8.75 millimeters. In some embodiments, the apertures 535 disposed in the interior portion 530 may have a diameter between about 1.8 millimeters to about 2.2 millimeters.

At least one of the apertures 535 in the periphery 525 of the sealing layer 412 may be positioned at the edges 545 of the periphery 525, and may have an interior cut open or exposed at the edges 545 that is in fluid communication in a lateral direction with the edges 545. The lateral direction may refer to a direction toward the edges 545 and in the same plane as the sealing layer 412. In some embodiments, the apertures 535 in the periphery 525 may be positioned proximate to or at the edges 545 and in fluid communication in a lateral direction with the edges 545. The apertures 535 positioned proximate to or at the edges 545 may be spaced substantially equidistant around the periphery 525. Alternatively, the spacing of the apertures 535 proximate to or at the edges 545 may be irregular.

Additionally, in some embodiments, the sealing layer 412 may further include one or more registration apertures, such as alignment holes 554, which may be useful for facilitating alignment of the manifold 408 and the sealing layer 412 during manufacturing and/or assembly of the tissue interface 108. For example, the alignment holes 554 may be positioned in corner regions of the interior border 550 of the sealing layer 412, such as alignment regions 558 that may otherwise be substantially free of apertures or holes. The exact number and positioning of the alignment holes 554 may vary; however, in some instances the alignment holes 554 may include two holes or apertures in each of the four corner regions of the interior border 550, for a total of eight holes. In some embodiments, the alignment holes 554 may be positioned adjacent to a set of three apertures 535 of the periphery 525, which may span along the curvatures of the four corners of the interior border 550.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 300 g/m^2 per twenty-four hours in some embodiments. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. In some embodiments, the cover may be a drape 406 shown in FIG. 4. In some embodiments, the drape 406 may have an opening 476 providing communication between the manifold 408 and the therapy cavity 403.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing interface 107 may facilitate coupling the negative-pressure source 104 to the dressing 102. The negative pressure provided by the negative-pressure source 104 may be delivered through the conduit 135 to a negative-pressure interface, which may include an elbow portion. In one illustrative embodiment, the negative-pressure interface may be a T.R.A.C.® Pad or Sensa T.R.A.C.® Pad available from KCI of San Antonio, Tex. The negative-pressure interface enables the negative pressure to be delivered through the cover 106 and to the tissue interface 108 and the tissue site. In this illustrative, non-limiting embodiment, the elbow portion may extend through the cover 106 to the tissue interface 108, but numerous arrangements are possible.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the pressure sensor 120 or the electric sensor 124, are generally known in the art as any apparatus operable to detect or measure a physical phenomenon or property, and generally provide a signal indicative of the phenomenon or property that is detected or measured. For example, the pressure sensor 120 and the electric sensor 124 may be configured to measure one or more operating parameters of the therapy system 100. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 124 may optionally measure operating parameters of the negative-pressure source 104, such as the voltage or current, in some embodiments. Preferably, the signals from the pressure sensor 120 and the electric sensor 124 are suitable as an input signal to the controller 110, but some signal conditioning may be appropriate in some embodiments. For example, the signal may need to be filtered or amplified before it can be processed by the controller 110. Typically, the signal is an electrical signal that is transmitted and/or received on by wire or wireless means, but may be represented in other forms, such as an optical signal.

The container 112 may also be representative of a container, canister, pouch, or other storage component, which can be used to collect and manage exudates and other fluids withdrawn from a tissue site. In many environments, a rigid container such as, for example, a container 162, may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may comprise a canister having a collection chamber, a first inlet fluidly coupled to the collection chamber and a first outlet fluidly coupled to the collection chamber and adapted to receive negative pressure from a source of negative pressure. In some embodiments, a first fluid conductor may comprise a first member such as, for example, the conduit 135 fluidly coupled between the first inlet and the tissue interface 108 by the negative-pressure interface described above, and a second member such as, for example, the conduit 126 fluidly coupled between the first outlet and a source of negative pressure whereby the first conductor is adapted to provide negative pressure within the collection chamber to the tissue site.

The therapy system 100 may also comprise a flow regulator such as, for example, a vent regulator 118 fluidly coupled to a source of ambient air to provide a controlled or managed flow of ambient air to the sealed therapeutic environment provided by the dressing 102 and ultimately the tissue site. In some embodiments, the vent regulator 118 may control the flow of ambient fluid to purge fluids and exudates from the sealed therapeutic environment. In some embodiments, the vent regulator 118 may be fluidly coupled by a fluid conductor or vent conduit 145 through the dressing interface 107 to the tissue interface 108. The vent regulator 118 may be configured to fluidly couple the tissue interface 108 to a source of ambient air as indicated by a dashed arrow. In some embodiments, the vent regulator 118 may be disposed within the therapy system 100 rather than being proximate to the dressing 102 so that the air flowing through the vent regulator 118 is less susceptible to accidental blockage during use. In such embodiments, the vent regulator 118 may be positioned proximate the container 112 and/or proximate a source of ambient air where the vent regulator 118 is less likely to be blocked during usage.

In operation, the tissue interface 108 may be placed within, over, on, or otherwise proximate a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

In one embodiment, the controller 110 may receive and process data, such as data related to the pressure distributed to the tissue interface 108 from the pressure sensor 120. The controller 110 may also control the operation of one or more components of therapy system 100 to manage the pressure distributed to the tissue interface 108 for application to the wound at the tissue site 150, which may also be referred to as the wound pressure (WP). In one embodiment, controller 110 may include an input for receiving a desired target pressure (TP) set by a clinician or other user and may be program for processing data relating to the setting and inputting of the target pressure (TP) to be applied to the tissue site 150. In one example embodiment, the target pressure (TP) may be a fixed pressure value determined by a user/caregiver as the reduced pressure target desired for therapy at the tissue site 150 and then provided as input to the controller 110. The user may be a nurse or a doctor or other approved clinician who prescribes the desired negative pressure to which the tissue site 150 should be applied. The desired negative pressure may vary from tissue site to tissue site based on the type of tissue forming the tissue site 150, the type of injury or wound (if any), the medical condition of the patient, and the preference of the attending physician. After selecting the desired target pressure (TP), the negative-pressure source 104 is controlled to achieve the target pressure (TP) desired for application to the tissue site 150.

As discussed above, the tissue site 150 may include, without limitation, any irregularity with a tissue, such as an open wound, surgical incision, or diseased tissue. The therapy system 100 is presented in the context of a tissue site that includes a wound that may extend through the epidermis and the dermis, and may reach into the hypodermis or subcutaneous tissue. The therapy system 100 may be used to treat a wound of any depth, as well as many different types of wounds including open wounds, incisions, or other tissue sites. The tissue site 150 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 150 may include removal of fluids originating from the tissue site 150, such as exudates or ascites, or fluids instilled into the dressing to cleanse or treat the tissue site 150, such as antimicrobial solutions.

As indicated above, the therapy system 100 may be packaged as a single, integrated unit such as a therapy system including all of the components shown in FIG. 1 that are fluidly coupled to the dressing 102. In some embodiments, an integrated therapy unit may include the negative-pressure source 104, the controller 110, the pressure sensor 120, and the container 112 which may be fluidly coupled to the dressing interface 107. In this therapy unit, the negative-pressure source 104 is indirectly coupled to the dressing interface 107 through the container 112 by conduit 126 and conduit 135, and the pressure sensor 120 is indirectly coupled to the dressing interface 107 by conduit 121 and conduit 155 as described above. In some embodiments, the negative pressure conduit 135 and the pressure sensing conduit 155 may be combined in a single fluid conductor that can be, for example, a multi-lumen tubing comprising a central primary lumen that functions as the negative pressure conduit 135 for delivering negative pressure to the dressing interface 107 and several peripheral auxiliary lumens that function as the pressure sensing conduit 155 for sensing the pressure that the dressing interface 107 delivers to the tissue interface 108. In this type of therapy unit wherein the pressure sensor 120 is removed from and indirectly coupled to the dressing interface 107, the negative pressure measured by the pressure sensor 120 may be different from the wound pressure (WP) actually being applied to the tissue site 150. Such pressure differences must be approximated in order to adjust the negative-pressure source 104 to deliver the pump pressure (PP) necessary to provide the desired or target pressure (TP). Moreover, such pressure differences and predictability may be exacerbated by viscous fluids such as exudates being produced by the tissue site.

In some embodiments, a pressure sensor may be integrated within the dressing interface 107 so that the pressure sensor is proximate the tissue interface 108 when disposed on the tissue site in order to provide a more accurate reading of the wound pressure (WP) being provided within the therapy environment of the dressing 102. The integrated pressure sensor may be used with or without the pressure sensor 120 that is a remote pressure sensor indirectly coupled to the dressing interface 107. In some example embodiments, the dressing interface 107 may comprise a housing having a therapy cavity that opens to the tissue site when positioned thereon. The integrated pressure sensor may have a sensing portion disposed within the therapy cavity along with other sensors including, for example, a temperature sensor, a humidity sensor, and a pH sensor. The sensors may be electrically coupled to the controller 110 outside the therapy cavity to provide data indicative of the pressure, temperature, humidity, and acidity properties within the therapeutic space of the therapy cavity. The sensors may be electrically coupled to the controller 110, for example, by wireless means. Systems, apparatuses, and methods described herein provide the advantage of more accurate measurements of these properties, as well as other significant advantages described below in more detail.

As indicated above, the dressing 102 may include the cover 106, the dressing interface 107, and the tissue interface 108. Referring now to FIGS. 4, 5A, 5B, 5C, 6A, 6B, and 7, a first dressing is shown comprising a dressing interface 400, the drape 406, and a tissue interface fluidly coupled to the dressing interface 400 through the opening 476 of the drape 406. The tissue interface may include the manifold 408 and the sealing layer 412 disposed adjacent a tissue site 410, all of which may be functionally similar in part to the dressing interface 107, the cover 106, and the tissue interface 108, respectively, as described above. In one example embodiment, the dressing interface 400 may comprise a housing 401 and a wall 402 disposed within the housing 401 wherein the wall 402 forms a recessed space or a therapy cavity 403 that opens to the manifold 408 when disposed at the tissue site 410 and a component cavity 404 opening away from the tissue site 410 of the upper portion of the dressing interface 400. In some embodiments, sensing portions of various sensors may be disposed within the therapy cavity 403, and electrical devices associated with the sensors may be disposed within the component cavity 404 and electrically coupled to the sensing portions through the wall 402. Electrical devices disposed within the component cavity 404 may include components associated with some example embodiments of the therapy system of FIG. 1. Although the dressing interface 400 and the therapy cavity 403 are functionally similar to the dressing interface 107 as described above, the dressing interface 400 further comprises the wall 402, the sensors, and the associated electrical devices described below in more detail. In some embodiments, the housing 401 may further comprise a neck portion or neck 407 fluidly coupled to a conduit 405. In some embodiments, the housing 401 may further comprise a flange portion or flange 409 having flow channels (see FIG. 8) configured to be fluidly coupled to the therapy cavity 403.

In some example embodiments, the neck 407 of the housing 401 may include portions of both the therapy cavity 403 and the component cavity 404. That portion of the neck 407 extending into the therapy cavity 403 is fluidly coupled to the conduit 405, while the portion extending into the component cavity 404 may contain some of the electrical devices. In some example embodiments, the conduit 405 may comprise a primary lumen or a negative pressure lumen 430 and separate auxiliary lumens such as, for example, a remote pressure sensing lumen 433 and a venting lumen 435 fluidly coupled by the neck 407 of the housing 401 to the therapy cavity 403. The negative pressure lumen 430 is similar to the negative pressure conduit 135 that may be coupled indirectly to the negative-pressure source 104. The venting lumen 435 is similar to the vent conduit 145 that may be fluidly coupled to the vent regulator 118 for purging fluids from the therapy cavity 403. The remote pressure sensing lumen 433 is similar to the pressure sensing conduit 155 that may be fluidly coupled directly or indirectly to the pressure sensor 120 by the conduit 121 for providing a remote measurement of the negative pressure in the therapy cavity 403 FIG. 4C provided by the negative pressure lumen 430.

In some embodiments, the component cavity 404 containing the electrical devices may be open to the ambient environment such that the electrical devices are exposed to the ambient environment. In other example embodiments, the component cavity 404 may be closed by a cover such as, for example, a cap 411 to protect the electrical devices. In still other embodiments, the component cavity 404 covered by the cap 411 may still be vented to the ambient environment to provide cooling to the electrical devices and a source of ambient pressure for a pressure sensor disposed in the therapy cavity 403 as described in more detail below. The dressing interface 400 may further comprise a drape ring 413 covering the circumference of the flange 409 and the adjacent portion of the drape 406 to seal the therapy cavity 403 of the housing 401 over the manifold 408 and the tissue site 410. In some embodiments, the drape ring 413 may comprise a polyurethane film including and an attachment device such as, for example, an acrylic, polyurethane gel, silicone, or hybrid combination of the foregoing adhesives (not shown) to attach the drape ring 413 to the flange 409 and the drape 406. The attachment device of drape ring 413 may be a single element of silicon or hydrocolloid with the adhesive on each side that functions as a gasket between the drape 406 and the flange 409. In some embodiments, the drape ring 413 may be similar to the cover 106 and/or the attachment device described above in more detail.

In some embodiments, a pressure sensor 416, humidity sensor 418, and a temperature that may be a component of the humidity sensor 418 (collectively referred to below as "the sensors") may be disposed in the housing 401 with each one having a sensing portion extending into the therapy cavity 403 of the housing 401 and associated electronics disposed within the component cavity 404. The housing 401 may include other types of sensors, or combinations of the foregoing sensors, such as, for example, oxygen sensors. In some example embodiments, the sensors may be coupled to or mounted on the wall 402 and electrically coupled to electrical components and circuits disposed within the component cavity 404 by electrical conductors extending through the wall 402. In some preferred embodiments, the electrical conductors extend through pathways in the wall 402 while keeping the therapy cavity 403 electrically and pneumatically isolated from the component cavity 404. For example, the wall 402 may comprise a circuit board 432 on which the electrical circuits and components may be printed or mounted. In some other examples, the circuit board 432 may be the wall 402 that covers an opening between the therapy cavity 403 and the component cavity 404 to pneumatically isolate the therapy cavity 403 from the component cavity 404.

In some embodiments, the electrical circuits and/or components associated with the sensors that are mounted on the circuit board 432 within the component cavity 404 may be electrically coupled to the controller 110 to interface with the rest of the therapy system 100 as described above. In some embodiments, for example, the electrical circuits and/or components may be electrically coupled to the controller 110 by a conductor that may be a component of the conduit 405. In some other preferred embodiments, a communications module 422 may be disposed in the component cavity 404 of the housing 401 and mounted on the circuit board 432 within the component cavity 404. Using a wireless communications module 422 has the advantage of eliminating an electrical conductor between the dressing interface 400 and the integrated portion of the therapy system 100 that may become entangled with the conduit 405 when in use during therapy treatments. For example, the electrical circuits and/or components associated with the sensors along with the terminal portion of the sensors may be electrically coupled to the controller 110 by wireless means such as an integrated device implementing Bluetooth® Low Energy wireless technology. More specifically, the communications module 422 may be a Bluetooth® Low Energy system-on-chip that includes a microprocessor (an example of the microprocessors referred to hereinafter) such as the nRF51822 chip available from Nordic Semiconductor. The communications module 422 may be implemented with other wireless technologies suitable for use in the medical environment.

In some embodiments, a voltage regulator 423 for signal conditioning and a power source 424 may be disposed within the component cavity 404 of the housing 401, and mounted on the circuit board 432. The power source 424 may be secured to the circuit board 432 by a bracket 426. The power source 424 may be, for example, a battery that may be a coin battery having a low-profile that provides a 3-volt source for the communications module 422 and the other electronic components within the component cavity 404 associated with the sensors. In some example embodiments, the sensors, the electrical circuits and/or components associated with the sensors, the wall 402 and/or the circuit board 432, the communications module 422, and the power source 424 may be integrated into a single package and referred to hereinafter as a sensor assembly 425 as shown in FIG. 6B. In some preferred embodiments, the wall 402 of the sensor assembly 425 may be the circuit board 432 itself as described above that provides a seal between tissue site 410 and the atmosphere when positioned over the opening between the therapy cavity 403 and the component cavity 404 of the housing 401 and functions as the wall 402 within the housing 401 that forms the therapy cavity 403.

Referring now to FIGS. 8A and 8B, a perspective view and a bottom view, respectively, of a bottom surface of the flange 409 facing the manifold 408 is shown. In some embodiments, the bottom surface may comprise features or channels to direct the flow of liquids and/or exudates away from the sensors out of the therapy cavity 403 into the negative pressure lumen 430 when negative pressure is being applied to the therapy cavity 403. In some embodiments, these channels may be molded into the bottom surface of the flange 409 to form a plurality of serrated guide channels 437, perimeter collection channels 438, and intermediate collection channels 439. The serrated guide channels 437 may be positioned and oriented in groups on bottom surface to directly capture and channel at least half of the liquids being drawn into the therapy cavity 403 with the groups of serrated guide channels 437, and indirectly channel a major portion of the balance of the liquids being drawn into the therapy cavity 403 between the groups of serrated guide channels 437. In addition, perimeter collection channels 438 and intermediate collection channels 439 redirect the flow of liquids that are being drawn in between the groups of serrated guide channels 437 that are radially-oriented to direct the flow of liquids into the guide channels 437. An example of this redirected flow is illustrated by bolded flow arrows 436. In some example embodiments, a portion of the housing 401 within the therapy cavity 403 may comprise a second set of serrated guide channels 427 spaced apart and radially-oriented to funnel liquids being drawn into the therapy cavity 403 from the flange 409 into the negative pressure lumen 430.

As indicated above, the sensor assembly 425 may comprise a pressure sensor 416, a humidity sensor 418, and a temperature sensor as a component of either the pressure sensor 416 or the humidity sensor 418. Each of the sensors may comprise a sensing portion extending into the therapy cavity 403 of the housing 401 and a terminal portion electrically coupled to the electrical circuits and/or components within the component cavity 404. Referring more specifically to FIGS. 4, 6A, 6B, and 7A-7D, the housing 401 may comprise a sensor bracket 441 that may be a molded portion of the housing 401 within the therapy cavity 403 in some embodiments. The sensor bracket 441 may be structured to house and secure the pressure sensor 416 on the circuit board 432 within the therapy cavity 403 of the sensor assembly 425 that provides a seal between tissue site 410 and the atmosphere as described above. In some embodiments, the pressure sensor 416 may be a differential gauge comprising a sensing portion 442 and a terminal portion or vent 443. The vent 443 of the pressure sensor 416 may be fluidly coupled through the circuit board 432 to the component cavity 404 and the atmosphere by a vent hole 444 extending through the circuit board 432. Because the component cavity 404 is vented to the ambient environment, the vent 443 of the pressure sensor 416 is able to measure the wound pressure (WP) with reference to the ambient pressure. The sensing portion 442 of the pressure sensor 416 may be positioned in close proximity to the manifold 408 to optimize fluid coupling and accurately measure the wound pressure (WP) at the tissue site 410. In some embodiments, the pressure sensor 416 may be a piezo-resistive pressure sensor having a pressure sensing element covered by a dielectric gel such as, for example, a Model TE 1620 pressure sensor available from TE Connectivity. The dielectric gel provides electrical and fluid isolation from the blood and wound exudates in order to protect the sensing element from corrosion or other degradation. This allows the pressure sensor 416 to measure the wound pressure (WP) directly within the therapy cavity 403 of the housing 401 proximate to the manifold 408 as opposed to measuring the wound pressure (WP) from a remote location. In some embodiments, the pressure sensor 416 may be a gauge that measures the absolute pressure that does not need to be vented.

In some embodiments, the pressure sensor 416 also may comprise a temperature sensor for measuring the temperature at the tissue site 410. In other embodiments, the humidity sensor 418 may comprise a temperature sensor for measuring the temperature at the tissue site 410. The sensor bracket 441 also may be structured to support the humidity sensor 418 on the circuit board 432 of the sensor assembly 425. In some embodiments, the humidity sensor 418 may comprise a sensing portion that is electrically coupled through the circuit board 432 to a microprocessor mounted on the other side of the circuit board 432 within the component cavity 404. The sensing portion of the humidity sensor 418 may be fluidly coupled to the space within the therapy cavity 403 that includes a fluid pathway 445 extending from the therapy cavity 403 into the negative pressure lumen 430 of the conduit 405 as indicated by the bold arrow to sense both the humidity and the temperature. The sensing portion of the humidity sensor 418 may be positioned within the fluid pathway 445 to limit direct contact with bodily fluids being drawn into the negative pressure lumen 430 from the tissue site 410. In some embodiments, the space within the therapy cavity 403 adjacent the sensing portion of the humidity sensor 418 may be purged by venting the space through the venting lumen 435 as described in more detail below. The space may also be flushed by instilling fluids into the space through the instillation lumen 433. As indicated above, the humidity sensor 418 may further comprise a temperature sensor (not shown) as the location within the fluid pathway 445 is well-suited to achieve accurate readings of the temperature of the fluids. In some embodiments, the humidity sensor 418 that comprises a temperature sensor may be a single integrated device such as, for example, Model TE HTU21D(F) humidity sensor also available from TE Connectivity.

In some example embodiments, the dressing 102 may further comprise one or more sensors adapted to be positioned between the sealing layer 412 and the tissue site 410. In some embodiments, the dressing 102 may include the manifold 408 by itself without a sealing layer and as such may comprise one or more sensors adapted to be positioned between the manifold 408 and the tissue site 410. The manifold 408 may be any one of the non-active advanced wound dressings described above including, without limitation, Tielle, KerraFoam, and dressings available from other companies. The sensors may include FTIR prismatic sensors, temperature sensors, MMP detecting sensors, pH sensors, or any other sensor which measures a property of the wound fluids which may be diagnostic of the healing rate or progression of the wound including the presence of infectious materials. The sensors may also include screen-printed biochemical sensors such as glucose, lactate, and glutamate.

In some embodiments, the dressing 102 may comprise multiple sensors disposed at different locations. For example, the dressing 102 comprising the sealing layer 412 and the manifold 408 may include a first sensor positioned adjacent the interior portion 530 of the sealing layer 412 or the manifold 408. The first sensor may be adapted to detect a property of fluid present at the tissue site 410 and to provide an output based on the property detected in the interior region of the tissue site 410. Some embodiments may further comprise a second sensor that may be positioned adjacent the periphery 525 of the sealing layer 412 or the manifold 408. The second sensor may also be adapted for detecting a property of the fluid present at the tissue site 410 and providing an output based on the property detected in the peripheral region of the tissue site 410. In some embodiments, the first and second sensors may be adapted to detect the same property or two different properties. In some embodiments, the dressing 102 may comprise multiple sensors at different locations around the periphery 525 of the sealing layer 412 or the manifold 408 wherein the multiple sensors are adapted to detect properties of the fluid present at multiple peripheral regions of the tissue site 410.

In some example embodiments, the first and second sensors may be pH sensors configured to detect a pH level of fluids present at the tissue site for providing a pH output based on the pH level detected at that particular location at the tissue site. In some embodiments, the dressing 102 may further comprise a pH sensor or pH sensors having a sensing portion adapted to be positioned between the sealing layer 412 or the manifold 408 and the tissue site 410 as described above. Referring more specifically to FIG. 4 and FIGS. 10A-10B, for example, the dressing 102 may comprise an interior pH sensor 414 having a head or a sensing portion 415 positioned adjacent the interior portion 530 of the sealing layer 412 and a peripheral pH sensor 417 having a head or a sensing portion 419 positioned adjacent the periphery 525 of the sealing layer 412. As indicated above, the dressing 102 may comprise multiple peripheral pH sensors at different locations around the periphery 525 of the sealing layer 412. For example, the peripheral pH sensor 417 may be positioned on a portion of the epidermis immediately adjacent the tissue site 410, such as at a periwound region, while a second peripheral pH sensor may be positioned on the epidermis at a greater distance away from the tissue site 410. In some embodiments, both the interior pH sensor 414 and the peripheral pH sensor 417 may be electrically coupled to the controller 110 through the sealing layer 412 and the manifold 408. Thus, by configuring the dressing 102 to include one or more pH sensors for detecting or measuring the pH at different locations within or outside of the tissue site 410, the controller 110 in conjunction with the other components of the therapy system 100 may be configured to determine whether a particular pH parameter is localized to a specific region of the tissue site 410 or the tissue surrounding the tissue site 410. The controller 110 may also be configured to compare pH measurements obtained from different locations throughout the tissue site 410 or the surrounding tissue.

Some embodiments of the pH sensors 414 and 417 may be electrically coupled through the sealing layer 412 and the manifold 408 to a front-end amplifier 421 mounted on the circuit board 432 within the component cavity 404. The interior pH sensor 414 may further comprise a terminal portion 428 electrically coupled to the sensing portion 415 by a conductor portion 478 extending through the sealing layer 412 and the manifold 408. The peripheral pH sensor 417 also may comprise a terminal portion 429 electrically coupled to the sensing portion 419 by a conductor portion 479 that also extends through the sealing layer 412 and the manifold 408. In some embodiments, the conductor portions 478 and 479 may be a flexible conductive material manufactured as a component of the sealing layer 412 and the manifold 408 separate from the sensing portions 415 and 419 and/or the terminal portions 428 and 429. In some other embodiments, the conductor portions 478 and 479 may be threaded through apertures extending through the sealing layer 412 and the manifold 408 when the dressing 102 is being applied to the tissue site 410 as described below. In yet other embodiments, the pH sensors 414 and 417 may have a bracket shape that is flexible and an integral component of the manifold 408 and/or the sealing layer 412 as shown in the figures. More specifically, the pH sensors 414 and 417 may be a single component comprising the sensing portions 415 and 419, the conductor portions 478 and 479, and the terminal portions 428 and 429 that are integral components of the sensors.

In some embodiments, the sensing portions 415 and 419 and/or the terminal portions 428 and 429, or portions thereof, may be printed on a thin polymer flexible circuit which insulates the sensing portions 415 and 419 and/or the terminal portions 428 and 429 and traverses the sealing layer 412 and the manifold 408. In some embodiments, the conductor portions 478 and 479, or portions thereof may also be printed on a thin polymer flexible circuit which insulates them and extend through the sealing layer 412 and the manifold 408. The thin polymer flexible circuit may comprise one or more individual conductors or wires depending on the type of pH sensor being utilized. For example, the pH sensors 414 and 417 each comprise two conductors extending from the sensing portions 415 and 419 through the conductor portions 478 and 479 to the terminal portions 428 and 429. In some embodiments, each of the two conductors may be exposed through the insulation to form a contact pad configured to be electrically coupled to electrical terminals associated with the dressing interface 400.

The conductors of the terminal portions 428 and 429 may be directly coupled to the front-end amplifier 421 by conductors or indirectly by other coupling means or components to facilitate the removal and replacement of the dressing interface 400 from the dressing 102 or the manifold 408. For example, one embodiment of a coupling means may comprise an electrical connector wherein each of the conductors of the terminal portions 428 and 429 include a pad or dressing terminal and the dressing interface 400 includes a contact or module terminal for connecting and disconnecting the terminal portions 428 and 429 from the front-end amplifier 421. In some embodiments, the coupling means may further comprise a mechanical coupler wherein the terminal portions 428 and 429 include a dressing coupler and the dressing interface 400 includes a module coupler for holding the dressing interface 400 in place on the manifold 408 in order to maintain electrical continuity of the electrical connector, i.e., the pad terminal and the contact terminal.

Referring to FIG. 10C, some embodiments of the interior pH sensor 414 may comprise a first electrical pad 501 and a second electrical pad 502 associated with the terminal portion 428 and the dressing interface 400 may comprise a first electrical contact 503 and a second electrical contact 504 mounted on the base of the dressing interface 400 and coupled to the front-end amplifier 421. The first electrical contact 503 may be configured to be electrically coupled to the first electrical pad 501 when the dressing interface 400 is positioned on the manifold 408. The second electrical contact 504 also may be configured to be electrically coupled to the second electrical pad 502 when the dressing interface 400 is positioned on the manifold 408. Some embodiments of the first electrical contact 503 and the second electrical contact 504 may include a spring-loaded mechanism (not shown) to further enhance the maintenance of electrical continuity. In some embodiments, the mechanical coupler may include a dressing coupler such as, for example, a magnetic attachment pad 511 mechanically coupled to the terminal portion 428 and a magnet 513 mounted on the base of the dressing interface 400. The magnetic attachment pad 511 and the magnet 513 may be embedded within the terminal portion 428 or the manifold 408 in some embodiments. The magnetic attachment pad 511 and the magnet 513 may be configured to align and connect the dressing interface 400 with the terminal portion 428 to achieve a good mechanical connection between them. A good mechanical connection is desirable in order to hold the dressing interface 400 in place and maintain electrical continuity between the first electrical pad 501 and the first electrical contact 503, as well as between the second electrical pad 502 and the second electrical contact 504, when the dressing interface 400 is positioned on the manifold 408. The surfaces and/or shapes of the electrical pads and the electrical contacts may also be configured to maintain good mechanical connection and electrical continuity. For example, the surface of the first electrical pad 501 may have a semicircular shape rather than a pad and the surface of the first electrical contact 503 may have a cup shape for receiving and aligning the first electrical contact 503 with the first electrical pad 501 when the dressing interface 400 is positioned on the manifold 408. The same may be applicable to the second electrical pad 502 and the second electrical contact 504. Referring back to FIGS. 4 and 10A, some embodiments of the peripheral pH sensor 417 may be substantially similar to the interior pH sensor 414 as described above.

In some embodiments, the connection means may further comprise an attachment device such as, for example, an adhesive ring (not shown) disposed between the manifold 408 and the base of the dressing interface 400. In some embodiments, the adhesive ring may be disposed on the base of the dressing interface 400 and include a protective release liner that would be removed before disposing the dressing interface on the manifold 408 including the pH sensors 414 and 417. In such embodiments, the drape 406 may also comprise an attachment device that holds the manifold 408 and the sealing layer 412 in place against the tissue site 410. The adhesive ring holds the dressing interface 400 in place to also provide a good mechanical connection and electrical continuity with the manifold 408 until the dressing interface 400 is removed. In this embodiment, the adhesive ring may have a removal force lower than a removal force of the manifold 408 from the tissue site 410 such that the dressing interface 400 may be removed from the manifold 408 with no damage to the dressing interface 400 or the manifold 408. In some embodiments, the adhesive ring may be a lightswitchable type device that is triggered to release by a signal provided to the dressing interface 400 and an integrated UV emitter and diffuser integrated within the dressing interface 400.

The conductor portions 478 and 479 of the interior pH sensor 414 and the peripheral pH sensor 417, respectively, extend through and exit the manifold 408 leaving perforations 488 and 489, respectively, as shown in FIG. 10A and 10C. These perforations are potential passageways for fluid leaks or bacterial contamination from wound fluid from the tissue site when in use. In some embodiments, the dressing interface 400 may be intended to function as a reusable module because of the expensive components, while the dressing or manifold 408 may intended to be replaceable and less costly. Thus, the manifold 408 must have an effective leakage/bacterial barrier to isolate the dressing interface 400 and associated electronics from being contaminated by the wound fluid. In some embodiments, the terminal portions 428 and 429 may comprise an adhesive backing (not shown) for sealing a portion of the perforations 488 and 489 created by the conductor portions 478 and 479, respectively. Some embodiments may further comprise a second covering of a bacterial membrane such as, for example, an adhesive drape 515 that covers the perforations 488 and 489 and the terminal portions 428 and 429 while maintaining electrical continuity between the first electrical pad 501 and the first electrical contact 503, as well as the second electrical pad 502 and the second electrical contact 504, respectively. In some embodiments, the adhesive drape 515 may have openings for the first and second electrical pads 501 and 502 and/or the magnetic attachment pad 511. In some embodiments, the magnetic attachment pad 511 may establish a good mechanical connection without the need for openings in the adhesive drape 515.

Referring more specifically to FIGS. 4 and 10C, some embodiments of the drape 406 may have an opening 476 as described above that encircles the terminal portions 428 and 429. In such embodiments, the leakage/bacterial barrier would further comprise the adhesive drape 515 would cover and seal both the drape 406 and the terminal portions 428 and 429 as described above. In some embodiments, the adhesive drape 515 may comprise a polyurethane film including and an attachment device such as, for example, an acrylic, polyurethane gel, silicone, or hybrid combination of the foregoing adhesives (not shown) to attach the adhesive drape 515 to the terminal portions 428 and 429 and the drape 406. The attachment device of adhesive drape 515 may be a single element of silicon or hydrocolloid with the adhesive on each side that functions as a gasket between the drape 406 and the terminal portions 428 and 429. In some embodiments, the adhesive drape 515 may be similar to the cover 106 and/or the attachment device described above in more detail.

Referring to FIG. 11, the therapy system 100 may comprise an electronics module 600 separate from the dressing interface 107 that may be located at a position different from the tissue interface 108. In some embodiments, the electronics module 600 may be substantially similar to the dressing interface 400 without the negative pressure delivery capability. More specifically, the electronics module 600 may comprise all the features of the dressing interface 400 described above, but may exclude the therapy cavity 403 and the neck 407 including the conduit 405 for delivering negative pressure to the therapy cavity 403. In some embodiments, the electronics module 600 may be a simple domed device that may be coupled to the tissue interface by terminal portions similar to the terminal portions 428 and

429 of the pH sensors 414 and 417 as described above. The pH sensors 414 and 417 may be wirelessly coupled to the other components of the therapy system 100 as described herein. Thus, the electronics module 600 provides the additional features allowing the module 600 to releasably engage the tissue interface 108 at different locations in order to measure the properties of fluids at those different locations and communicate related information within the therapy system 100 while remaining fluidly isolated from the tissue interface 108.

The terminal portions 428 and 429 may each include more than one magnetic couplers wherein the terminal portions 428 and 429 each include two dressing couplers and the dressing interface 400 includes two module couplers to better hold the dressing interface 400 firmly on the manifold 408 in order to maintain electrical continuity of the electrical connector, i.e., the pad terminal and the contact terminal. For example, a terminal portion 628 similar to the terminal portion 428 may comprise two dressing couplers that may be magnetic attachments 611 and 612 and two module couplers that may be magnets 613 and 614. These two magnetic couplers may establish better electrical continuity for the electrical connectors 501/503 and 502/504 and provide stronger mechanical coupling between the terminal portion 628 and the dressing interface 400. The same is true for terminal portion 429 (but not shown) that may include more than one magnetic coupler as well.

Referring back to FIGS. 4 and 10C, the first and second electrical contacts 503 and 504 of the terminal portion 428 may be electrically coupled to the front-end amplifier 421 through the dressing interface 400 (not shown). The electrical contacts of the terminal portion 429 also may be electrically coupled to the front-end amplifier 421 and a similar fashion. In some embodiments, the first and second electrical contacts 503 and 504 may be electrically coupled by separate wires or may be combined into a single conduit that may be electrically coupled to the front-end amplifier 421. The front-end amplifier 421 may comprise analog signal conditioning circuitry that includes sensitive analog amplifiers such as, for example, operational amplifiers and application-specific integrated circuits. The front-end amplifier 421 measures minute voltage changes provided by the sensing portions to provide an output signal indicative of the pH of the fluids within or surrounding the tissue site 410. The front-end amplifier 421 may be, for example, an extremely accurate voltmeter that measures the voltage potential between the working electrode 451 and the reference electrode 452. The front-end amplifier 421 may be for example a high impedance analog front-end (AFE) device such as the LMP7721 and LMP91200 chips that are available from manufacturers such as Texas Instruments or the AD7793 and AD8603 chips that are available from manufacturers such as Analog Devices.

Measuring the pH level of the fluids within or surrounding the tissue site 410 is an important indicator of wound health. For example, a slightly acidic pH level between about 4.5 and about 6.5, may be considered as being optimal for wound healing in some embodiments, while a pH level outside this range, and particularly an alkaline pH level, may indicate that the wound has stalled. Separate equipment or instruments used to measure the pH level externally that are not integrated into the dressing have been used to measure the pH level of the wound during dressing changes that may occur, for example, every three days which provides infrequent data that is insufficient to form detailed trend information at one location in the wound or information at multiple locations in and around the wound, especially over large wound areas. By placing the pH sensors within the dressing itself between the sealing layer 412 and the tissue site 410 underneath the tissue interface 108 for measuring the pH level during the application of negative pressure therapy rather than during dressing changes, the pH level can be measured more frequently such as, for example every five minutes. As a result, valuable information regarding the healing process may be obtained that is sufficient to define trends at a single location and/or identify variations between different locations at the tissue site 410. Positioning the pH sensors in direct contact with the tissue site underneath such tissue interfaces described above may provide a more accurate measurement of the pH level.

Additionally, the therapy system 100 and/or the microprocessor of the communications module 422 may be programmed to detect the time rate of change of the pH to provide additional information regarding the healing process. In one example embodiment, the dressing interface 400 may further comprise an indicator 560 electrically coupled to the microprocessor of the communication module 422 to provide a visual indication indicating that there may be an unfavorable change of the pH and/or temperature of the wound or the skin that may indicate the presence of an infection. For example, the therapy system 100 may be programmed to provide a warning from the indicator 560 when the time rate of change from the acidic pH is more than about 20% over a 12 hour period. The indicator 560 may provide a visual, audible, or any other indication to warn the user or the caregiver.

Referring back to FIGS. 9A and 9B, the sensing portions 415 and 419 of the interior pH sensor 414 and/or the peripheral pH sensor 417, respectively, may be pH sensor 450 in some embodiments. The pH sensor 450 comprises a pair of printed medical electrodes including a working electrode 451 and a reference electrode 452. In some embodiments, the working electrode 451 may have a node being substantially circular in shape at one end and having a terminal portion at the other end. The reference electrode 452 may have a node substantially semicircular in shape and disposed around the node of the working electrode 451, and also may have a terminal portion at the other end. In some example embodiments, the working electrode 451 may comprise a material selected from a group including graphene oxide ink, conductive carbon, carbon nanotube inks, silver, nano-silver, silver chloride ink, gold, nano-gold, gold-based ink, metal oxides, conductive polymers, or a combination thereof. This working electrode 451 further comprise a coating or film applied over the material wherein such coating or film may be selected from a group including metal oxides such as, for example, tungsten, platinum, iridium, ruthenium, and antimony oxides, or a group of conductive polymers such as polyaniline and others so that the conductivity of the working electrode 451 changes based on changes in hydrogen ion concentration of the fluids being measured or sampled. In some example embodiments, the reference electrode 452 may comprise a material selected from a group including silver, nano-silver, silver chloride ink, or a combination thereof. The pH sensor 450 may further comprise a coating 453 covering the electrodes that insulates and isolates the working electrode 451 from the reference electrode 452 and the wound fluid, except for an electrically conductive space 454 between the nodes of the working electrode 451 and the reference electrode 452. In some embodiments, the coating 453 does not completely cover the terminal portions of the working electrode 451 and the reference electrode 452 to form terminals 455 and 456, respectively. In some embodiments, the terminals 455 and

456 may be electrically coupled to the front-end amplifier 421 through the conductor portions 478 and 479 and the terminal portions 428 and 429, respectively, by the corresponding electrical conductors such as, for example, the electrical conductors 501/503 and 502/504 of the terminal portion 428.

In some other embodiments, the sensing portions 415 and 419 of the interior pH sensor 414 and/or the peripheral pH sensor 417 may include a third electrode such as, for example, pH sensor 460 shown in FIG. 9B, and hence a third electrical connector for each one of the terminal portions 428 and 429. In some embodiments, the pH sensor 460 comprises a counter electrode 462 in addition to the working electrode 451 and the reference electrode 452 of the pH sensor 450. The counter electrode 462 also comprises a node partially surrounding the node of the working electrode 451 and a terminal 466 adapted to be electrically coupled to the front-end amplifier 421. Otherwise, the pH sensor 460 is substantially similar to the pH sensor 450 described above as indicated by the reference numerals. The counter electrode 462 is also separated from the working electrode 451 and is also insulated from the wound fluid and the other electrodes by the coating 453 except in the conductive space 454. The counter electrode 462 may be used in connection with the working electrode 451 and the reference electrode 452 for the purpose of error correction of the voltages being measured. For example, the counter electrode 462 may possess the same voltage potential as the potential of the working electrode 451 except with an opposite sign so that any electrochemical process affecting the working electrode 451 will be accompanied by an opposite electrochemical process on the counter electrode 462. Although voltage measurements are still being taken between the working electrode 451 and the reference electrode 452 by the analog front end device of the pH sensor 460, the counter electrode 462 may be used for such error correction and may also be used for current readings associated with the voltage measurements. Custom printed electrodes assembled in conjunction with a front-end amplifier may be used to partially comprise pH sensors such as the pH sensor 450 and the pH sensor 460 may be available from several companies such as, for example, GSI Technologies, Inc. and Dropsens.

In some embodiments, the tissue interfaces described above may comprise a film underside such as, for example, the sealing layer 412. In some embodiments, the sensing portion of the pH sensors may be printed directly on the sealing layer 412 to form a thin and flexible sensor or a separate film layer having a smooth surface (not shown). The separate layer may be, for example, another polyurethane film which is then bonded to the sealing layer 412. In some embodiments, the sensing portion of the pH sensors may be screen-printed onto a separate mylar (PET) substrate or directly onto the polyurethane sealing layer utilizing silver chloride, graphene, or other conductive inks, for example. Additional perforations or apertures may be formed in the sealing layer 412 to ensure adequate fluid flow around the sensing portion of the pH sensor. However, some preferable embodiments do not include any perforations or apertures in the region of the sensing portions 415 and 419 of the pH sensors 414 and 417 to avoid impacting the conduction of the electrically conductive space 454 between the nodes of the working electrode 451 and the reference electrode 452.

In some other example embodiments, the tissue interface may comprise a smooth surface integrated with the tissue-facing side of a manifold such as, for example, the manifold 408 that may include a smooth surface underneath (not shown). In such embodiments, the pH sensors may be printed directly on the smooth surface of the manifold to form a tissue interface integrated with the pH sensors. In some embodiments, the pH sensors 414 and 417 may be screen-printed directly onto the smooth surface of the manifold 408 utilizing silver chloride, graphene, or other conductive inks, for example, as described above.

The pH sensors may be positioned at various pH sites within the interior portion 530 and around the periphery 525 of the sealing layer 412, as well as in the periwound region. In some embodiments, each of these pH sensors may be printed as an array of individual pH sensors positioned at the pH sites and/or as an array of individual pH sensors at each of the pH sites. In such embodiments, each of the individual pH sensors may be electrically coupled to front-end amplifier 421 as described above.

The systems, apparatuses, and methods described herein may provide other significant advantages. For example, some therapy systems are a closed system wherein the pneumatic pathway is not vented to ambient air, but rather controlled by varying the supply pressure (SP) to achieve the desired target pressure (TP) in a continuous pressure mode, an intermittent pressure mode, or a variable target pressure mode as described above in more detail with reference to FIGS. 2 and 3. In some embodiments of the closed system, the wound pressure (WP) being measured in the dressing interface 107 may not drop in response to a decrease in the supply pressure (SP) as a result of a blockage within the dressing interface 107 or other portions of the pneumatic pathway. In some embodiments of the closed system, the supply pressure (SP) may not provide airflow to the tissue interface 108 frequently enough that may result in the creation of a significant head pressure or blockages within the dressing interface 107 that also would interfere with sensor measurements being taken by the dressing interface 400 as described above. The head pressure in some embodiments may be defined as a difference in pressure (DP) between a negative pressure set by a user or caregiver for treatment, i.e., the target pressure (TP), and the negative pressure provided by a negative pressure source that is necessary to offset the pressure drop inherent in the fluid conductors, i.e., the supply pressure (SP), in order to achieve or reach the target pressure (TP). For example, the head pressure that a negative pressure source needs to overcome may be as much as 75 mmHg. Problems may occur in such closed systems when a blockage occurs in the pneumatic pathway of the fluid conductors that causes the negative pressure source to increase to a value above the normal supply pressure (SP) as a result of the blockage. For example, if the blockage suddenly clears, the instantaneous change in the pressure being supplied may cause harm to the tissue site.

Some therapy systems have attempted to compensate for head pressure by introducing a supply of ambient air flow into the therapeutic environment, e.g., the therapy cavity 403, by providing a vent with a filter on the housing 401 of the dressing interface 400 to provide ambient air flow into the therapeutic environment as a controlled leak. In some instances, however, the filter may be blocked when the interface dressing is applied to the tissue site or when asked at least blocked during use. Locating the filter in such a location may also be problematic because it is more likely to be contaminated or compromised by other chemicals and agents associated with treatment utilizing instillation fluids that could adversely affect the performance of the filter and the vent itself The embodiments of the therapy systems described herein overcome the problems associated with having a large head pressure in a closed pneumatic environment, and the problems associated with using a vent disposed on or adjacent the dressing interface. More specifically, the embodiments of the therapy systems described above comprise a pressure sensor, such as the pressure sensor 416, disposed within the pneumatic environment, i.e., in situ, that independently measures the wound pressure (WP) within the therapy cavity 403 of the housing 401 as described above rather than doing so remotely. Consequently, the pressure sensor 416 is able to instantaneously identify dangerously high head pressures and/or blockages within the therapy cavity 403 adjacent the manifold 408. Because the auxiliary lumens are not being used for pressure sensing, the venting lumen 435 may be fluidly coupled to a fluid regulator such as, for example, the vent regulator 118 in FIG. 1, that may remotely vent the therapeutic environment within the therapy cavity 403 to the ambient environment or fluidly couple the therapeutic environment to a source of positive pressure. The vent regulator 118 may then be used to provide ambient air or positive pressure to the therapeutic environment in a controlled fashion to "purge" the therapeutic environment within both the therapy cavity 403 to resolve the problems identified above regarding head pressures and blockages.

In embodiments of therapy systems that include an air flow regulator comprising a valve such as the solenoid valve described above, the valve provides controlled airflow venting or positive pressure to the therapy cavity 403 as opposed to a constant airflow provided by a closed system or an open system including a filter in response to the wound pressure (WP) being sensed by the pressure sensor 416. The controller 110 may be programmed to periodically open the solenoid valve as described above allowing ambient air to flow into the therapy cavity 403, or applying a positive pressure into the therapy cavity 403, at a predetermined flow rate and/or for a predetermined duration of time to purge the pneumatic system including the therapy cavity 403 and the negative pressure lumen 430 of bodily liquids and exudates so that the humidity sensor 418 and the pH sensors 414 and 417 provide more accurate readings and in a timely fashion. This feature allows the controller to activate the solenoid valve in a predetermined fashion to purge blockages and excess liquids that may develop in the fluid pathways or the therapy cavity 403 during operation. In some embodiments, the controller may be programmed to open the solenoid valve for a fixed period of time at predetermined intervals such as, for example, for five seconds every four minutes to mitigate the formation of any blockages.

In operation, the tissue interface 108 may be placed within, over, on, or otherwise proximate a tissue site, such as tissue site 150. The cover 106 may be placed over the tissue interface 108 and sealed to an attachment surface near the tissue site 150. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment.

Some embodiments of therapy systems including, for example, the therapy system 100 including the dressing 102, are illustrative of a method for providing reduced-pressure to a tissue interface and sensing properties of fluids extracted from a tissue site for treating the tissue. In one example embodiment, the method may comprise positioning a tissue interface on the tissue site, wherein the tissue interface has a first layer comprising foam and a second layer comprising a plurality of apertures. In some embodiments, the second layer may be adapted to be positioned between the first layer and the tissue site. In some embodiments, the method may further comprise positioning a sensing portion of a pH sensor between the second layer and the tissue site. In some embodiments, the method may further comprise positioning an opening of a dressing interface on the first layer, wherein the dressing interface includes a housing having a therapy cavity including the opening and a component cavity fluidly isolated from the therapy cavity. In some embodiments, the method may further comprise electrically coupling the pH sensor to a microprocessor disposed within the component cavity. In some embodiments, the method may further comprise detecting a pH level of fluid present at the tissue site based on a pH output provided by the first pH sensor to the microprocessor based on the pH level detected.

The dressing interface may further comprise a temperature sensor, a humidity sensor, and a pressure sensor, each having a sensing portion disposed within the therapy cavity and each electrically coupled to the microprocessor. The method may further comprise applying reduced pressure to the therapy cavity to draw fluids from the tissue interface into the therapy cavity and out of a reduced-pressure port. The method may further comprise sensing the pH, temperature, humidity, and pressure properties of the fluids flowing through therapy cavity utilizing the sensing portion of the sensors and outputting signals from the sensors to the microprocessor. The method may further comprise providing fluid data from the microprocessor indicative of such properties, and inputting the fluid data from the control device to the therapy system for processing the fluid data and treating the tissue site in response to the fluid data.

The systems, apparatuses, and methods described herein may provide other significant advantages over dressing interfaces currently available. For example, an advantage of using the dressing interface 400 that includes a pressure sensor in situ such as, for example, the pressure sensor 416, is that the pressure sensor 416 can more accurately monitor the wound pressure (WP) at the tissue site and identify blockages and fluid leaks that may occur within the therapeutic space as described in more detail above. Another advantage of using a dressing interface including in situ sensors, e.g., the dressing interface 400, is that the sensor assembly 425 provides additional data including pressure, temperature, humidity, and pH of the fluids being drawn from the tissue site that facilitates improved control algorithms and wound profiling to further assist the caregiver with additional information provided by the therapy unit of the therapy system to optimize the wound therapy being provided and the overall healing progression of the tissue site when combined with appropriate control logic.

The disposable elements can be combined with the mechanical elements in a variety of different ways to provide therapy. For example, in some embodiments, the disposable and mechanical systems can be combined inline, externally mounted, or internally mounted. In another example, the dressing interface 400 may be a disposable element that is fluidly coupled to a therapy unit of a therapy system as described in more detail above.

While shown in a few illustrative embodiments, a person having ordinary skill in the art will recognize that the systems, apparatuses, and methods described herein are susceptible to various changes and modifications. For example, certain features, elements, or aspects described in the context of one example embodiment may be omitted, substituted, or combined with features, elements, and aspects of other example embodiments. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A dressing for treating a tissue site, comprising:
a wound dressing including a foam layer having a tissue-facing surface and an opposing surface;
a dressing interface having a housing including a therapy cavity and a component cavity having an electrical component fluidly isolated from the therapy cavity and the wound dressing;
a sensor having a sensing portion positioned on the tissue-facing surface and adapted to contact the tissue site, a conductor portion coupled to the sensing portion and extending through a perforation in the wound dressing, and a terminal portion positioned on the opposing surface and coupled to the conductor portion, the terminal portion being configured to be electrically coupled to the electrical component;
an electrical connector adapted to electrically couple the terminal portion to the electrical component;
a mechanical coupler adapted to couple the dressing interface to the wound dressing and enhance the continuity of the electrical connector, the mechanical coupler comprising a magnetic attachment coupled to the terminal portion and a magnet disposed on the dressing interface within the therapy cavity and is releasably engageable to the magnetic attachment; and
a drape having an opening exposing the terminal portion and coupled to the opposing surface and covering the wound dressing and the tissue site to fluidly isolate the terminal portion from the wound dressing and the perforation.

2. The dressing of claim 1, the sensor is a pH sensor adapted to be electrically coupled to a microprocessor and further adapted to provide a pH output to the microprocessor based on the pH level detected.

3. The dressing of claim 2, wherein the pH sensor is electrically coupled to the microprocessor by a wireless communication device disposed in the dressing interface.

4. The dressing of claim 1, wherein the electrical connector comprises an electrical pad coupled to the terminal portion and an electrical contact disposed on the dressing interface, wherein the electrical contact is electrically coupled to the electrical component and releasably connectable to the electrical pad.

5. The dressing of claim 1, further comprising a port into the therapy cavity of the dressing interface and adapted to be fluidly coupled to a negative-pressure source and the therapy cavity in fluid communication with the wound dressing.

6. A method of applying negative-pressure to a dressing for treating a tissue site, the method comprising:

positioning a tissue interface on the tissue site, the tissue interface having a first layer comprising a foam and a second layer comprising a plurality of apertures, the second layer adapted to be positioned between the first layer and the tissue site;

positioning a sensing portion of a pH sensor between the second layer and the tissue site and extending a conductor portion of the pH sensor through the tissue interface;

positioning a drape having an opening over the tissue interface to cover the tissue interface and the tissue site;

positioning a dressing interface adjacent the drape and the tissue interface wherein the dressing interface has a therapy cavity fluidly coupled to the first layer of the tissue interface and a component cavity fluidly isolated from the therapy cavity;

electrically coupling a terminal portion of the pH sensor to an electrical component disposed within the component cavity with an electrical connector, wherein the terminal portion is coupled to the conductor portion disposed on the first layer, the terminal portion being exposed through the opening in the drape, the drape further isolating the tissue interface from the terminal portion;

mechanically coupling the dressing interface to the tissue interface to enhance the continuity of the electrical connector by coupling a magnetic attachment on the terminal portion to a magnet disposed on the dressing interface within the therapy cavity, the magnet being releasably engageable to the magnetic attachment; and applying negative pressure to the therapy cavity through a port to draw fluid from the tissue site, through the tissue interface, and into the therapy cavity.

7. A dressing for treating a tissue site, comprising:

a tissue interface having a first layer comprising a foam and a second layer comprising a plurality of apertures, the second layer adapted to be positioned between the first layer and the tissue site;

a dressing interface having a housing including a therapy cavity and a component cavity fluidly isolated from the therapy cavity, the therapy cavity having an opening adapted to be in fluid communication with the first layer and a port adapted to be fluidly coupled to a negative-pressure source;

a control device disposed within the component cavity and including a microprocessor;

a first pH sensor having a sensing portion adapted to be positioned between the second layer and the tissue site and a terminal portion electrically coupled to the microprocessor, the first pH sensor configured to detect a pH level of fluid present at the tissue site and to provide a pH output to the microprocessor based on the pH level detected;

an electrical connector adapted to electrically couple the terminal portion to the microprocessor;

a mechanical coupler adapted to couple the dressing interface to the tissue interface and enhance the continuity of the electrical connector, the mechanical coupler comprising a magnetic attachment coupled to the terminal portion and a magnet disposed on the dressing interface within the therapy cavity and is releasably engageable to the magnetic attachment; and a drape having an opening exposing the terminal portion and coupled to the first layer and covering the tissue interface and the tissue site to fluidly isolate the terminal portion from the tissue interface.

8. The dressing of claim 7, further comprising a second pH sensor having a sensing portion adapted to be positioned between the second layer and the tissue site and electrically coupled to the microprocessor, the second pH sensor configured to detect a pH level of fluid present at the tissue site and to provide a pH output to the microprocessor based on the pH level detected.

9. The dressing of claim 8, wherein the first layer comprises a central area and a peripheral area, and wherein the sensing portion of the first pH sensor is adapted to be positioned adjacent the central area and the sensing portion of the second pH sensor is adapted to be positioned adjacent the peripheral area.

10. The dressing of claim 9, wherein the sensing portion of the second pH sensor is adapted to be positioned adjacent periwound tissue of the tissue site.

11. The dressing of claim 9, wherein the control device further comprises a wireless transmitter coupled to the microprocessor for communicating information regarding the pH outputs provided by the first pH sensor and the second pH sensor.

12. The dressing of claim 7, wherein the foam is reticulated polymer foam.

13. The dressing of claim 7, wherein the foam is hydrophobic.

14. The dressing of claim 7, wherein:

the first layer comprises silicone; and the second layer comprises a polyethylene film.

15. The dressing of claim 7, further comprising a cover adapted to be positioned between the dressing interface and the first layer of the tissue interface.

16. The dressing of claim 7, further comprising a vent port fluidly coupled to the therapy cavity and adapted to enable airflow into the therapy cavity.

17. The dressing of claim 7, further comprising a humidity sensor having a sensing portion adapted to be disposed within the therapy cavity and electrically coupled to the microprocessor, the humidity sensor configured to detect a humidity level of fluid present at the tissue site and to provide a humidity output to the microprocessor based on the humidity level detected.

18. The dressing of claim 7, further comprising a temperature sensor having a sensing portion adapted to be disposed within the therapy cavity and electrically coupled to the microprocessor, the temperature sensor configured to detect a temperature level of fluid present at the tissue site and to provide a temperature output to the microprocessor based on the temperature level detected.

19. The dressing of claim 7, further comprising a pressure sensor having a sensing portion adapted to be disposed within the therapy cavity and electrically coupled to the microprocessor, the pressure sensor configured to detect a pressure level of fluid present at the tissue site and to provide a pressure output to the microprocessor based on the pressure level detected.

20. The dressing of claim 7, further comprising a front-end amplifier disposed within the component cavity and electrically coupled between the first pH sensor and the microprocessor.

21. The dressing of claim 7, wherein the control device further comprises a wireless transmitter coupled to the microprocessor for communicating information regarding the pH output.

22. The dressing of claim 7, wherein the second layer comprises a central area and a peripheral area, and wherein the apertures in the peripheral area are larger than the apertures in the central area.

* * * * *